(12) United States Patent
El Ali et al.

(10) Patent No.: US 10,377,723 B2
(45) Date of Patent: *Aug. 13, 2019

(54) SOLID-SUPPORTED CATALYST FOR CROSS-COUPLING

(71) Applicant: KING FAHD UNIVERSITY OF PETROLEUM AND MINERALS, Dhahran (SA)

(72) Inventors: Bassam El Ali, Dhahran (SA); Rami Khalid Suleiman, Dhahran (SA); Mansur Bala Ibrahim, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,386

(22) Filed: Feb. 1, 2019

(65) Prior Publication Data
US 2019/0161457 A1 May 30, 2019

Related U.S. Application Data

(63) Continuation of application No. 15/362,997, filed on Nov. 29, 2016, now Pat. No. 10,280,147.
(60) Provisional application No. 62/313,849, filed on Mar. 28, 2016.

(51) Int. Cl.
| | | |
|---|---|---|
| *B01J 31/18* | (2006.01) |
| *C07D 263/14* | (2006.01) |
| *C07F 15/00* | (2006.01) |
| *C07C 1/32* | (2006.01) |
| *C07C 2/86* | (2006.01) |
| *C07C 45/68* | (2006.01) |
| *C07C 201/12* | (2006.01) |
| *C07D 317/50* | (2006.01) |
| *C07D 263/12* | (2006.01) |
| *C07C 41/30* | (2006.01) |
| *C07C 209/68* | (2006.01) |
| *C07C 253/30* | (2006.01) |
| *C07C 17/269* | (2006.01) |
| *C07C 41/32* | (2006.01) |

(52) U.S. Cl.
CPC .......... *C07D 263/14* (2013.01); *B01J 31/183* (2013.01); *C07C 1/321* (2013.01); *C07C 2/861* (2013.01); *C07C 17/269* (2013.01); *C07C 41/30* (2013.01); *C07C 41/32* (2013.01); *C07C 45/68* (2013.01); *C07C 201/12* (2013.01); *C07C 209/68* (2013.01); *C07C 253/30* (2013.01); *C07D 263/12* (2013.01); *C07D 317/50* (2013.01); *C07F 15/0066* (2013.01); *B01J 2231/4211* (2013.01); *B01J 2231/4261* (2013.01); *B01J 2231/4266* (2013.01); *B01J 2531/824* (2013.01)

(58) Field of Classification Search
CPC .......................... B01J 31/183; B01J 2531/824
See application file for complete search history.

(56) References Cited

U.S. PATENT DOCUMENTS

2017/0275318 A1* 9/2017 El Ali .................. C07D 263/14

FOREIGN PATENT DOCUMENTS

WO WO 2011/106992 A1 9/2011

OTHER PUBLICATIONS

S. Hiraoka, et al., "Electrostatically Controlled Hierarchical Arrangement of Monocationic Silver(I) and Dicationic Mercury(II) Ions between Disk-Shaped Template Ligands" American Chemical Society, 2006, vol. 128, No. 40, pp. 13038-13039.
M.B. Ibrahim, et al., "Effective palladium(II)-bis(oxazoline) catalysts: synthesis, crystal structure, and catalytic coupling reactions" Journal of Coordination Chemistry, Jan. 9, 2015, pp. 433-448.
S.M.Hussain, et al., "Palladium—bis(oxazoline) complexes with inherent chirality: Synthesis, crystal structures and applications in Suzuki, Heck and Sonogashira coupling reactions" Polyhedron, 2014, vol. 70 pp. 36-46.
V. Polshettiwar, et al., "PdeN-heterocyclic carbene (NHC) organic silica: synthesis nd application in carbon-carbon coupling reactions" Tetrahedron, vol. 64, 2008, pp. 4637-4643.
Suzuka, et al., "Reusable Polymer-Supported Terpyridine Palladium Complex for Suzuki-Miyaura, Mizoroki-Heck, Sonogashira, and Tsuji-Trost Reaction in Water" Polymers, 2011, vol. 3, pp. 621-639.
M. Bakherad, et al., "Solvent-free Heck and copper-free Sonogashira cross-coupling reactions catalyzed by a polystyrene-anchored Pd(II) phenyldithiocarbazate complex" Tetrahedron Letters, vol. 53, 2012, pp. 5773-5776.
H.Gruber-Woelfler, et al., "Synthesis, catalytic activity, and leaching studies of a heterogeneous Pd-catalyst including an immobilized bis(oxazoline) ligand" Journal of Catalysis, vol. 286, 2012, pp. 30-40.
K. Balaswamy, et al., "Polystyrene-supported palladium(II) N,N-dimethylethylenediamine complex: A recyclable catalyst for Suzuki—Miyaura cross-coupling reactions in water" Inorganica Chimica Acta, vol. 423, 2014, pp. 95-100.
M.M.Heravi, et al., "PdCl2 on modified poly(styrene-co-maleic anhydride): A highly active and recyclable catalyst for the Suzuki—Miyaura and Sonogashira reactions" Journal of Molecular Catalysis A: Chemical, vol. 394, 2014, pp. 74-82.
S. Das, et al., "Suzuki cross-coupling reaction over Pd-Schiff-base anchored mesoporous silica catalyst" Journal of Molecular Catalysis A: Chemical, vol. 394,2014, pp. 188-197.
S.M. Sarkar, et al., "Pyridinyl functionalized MCM-48 supported highly active heterogeneous palladium catalyst for cross-coupling reactionst" Royal Society of Chemistry, 2015, vol. 5 , pp. 19630-19637.
T. Baran, et al., "Carboxymethyl chitosan Schiff base supported heterogeneous palladium(II) catalysts for Suzuki cross-coupling reaction" Journal of Molecular Catalysis A: Chemical, vol. 407, 2015, pp. 47-52.
Ibrahim et al. "A palladium-bisoxazoline supported catalyst for selective synthesis of aryl esters and aryl amides via carbonylative coupling reactions" RSC Advances, 2016, vol. 6, pp. 78826-78837.
* cited by examiner

*Primary Examiner* — Joseph R Kosack
(74) *Attorney, Agent, or Firm* — Oblon, McClelland, Maier & Neustadt, L.L.P.

(57) ABSTRACT

A solid-supported catalyst ligand which chelates palladium (II) species to form a complex that functions as a heterogeneous catalyst that is stable and can be recycled without significantly losing any catalytic activity in a variety of chemical transformations, a method for producing the solid-supported catalyst ligand and a method for catalyzing a palladium cross-coupling reaction, such as the Suzuki-Miyaura, Mizoroki-Heck, and Sonagashira reactions.

6 Claims, 7 Drawing Sheets

SOLID-SUPPORTED CATALYST FOR CROSS-COUPLING

CROSS REFERENCE TO RELATED APPLICATIONS

This application is a Continuation of Ser. No. 15/362,997, now allowed, having a filing date of Nov. 29, 2016 which claims the benefit of priority from U.S. Provisional Application No. 62/313,849 filed on Mar. 28, 2016, the entire contents of which are incorporated herein by reference.

BACKGROUND OF THE INVENTION

Technical Field

The present disclosure relates to a solid-supported catalyst ligand and palladium (II) complexes and catalyst compositions thereof. Additionally, the present disclosure relates to methods for producing the solid-supported catalyst ligand and methods employing its complexes to catalyze chemical transformations including palladium cross-coupling reactions.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Catalytic cross coupling reactions have been recognized among the best direct routes for the formation of carbon-carbon bonds [G. Zhang, Y. Luan, X. Han, Y. Wang, X. Wen, C. Ding, *Appl. Organomet. Chem.* 2014, 28, 332.—incorporated herein by reference in its entirety]. Palladium complexes have been the most effective and versatile catalysts for the synthesis of biphenyls (Suzuki-Miyaura cross coupling reactions), internal alkenes, and alkynes (Mizoroki-Heck and Sonogashira cross coupling reactions) [H. U. Blaser, A. Indolese, A. Schnyder, H. Steiner, M. Studer, *J. Mol. Cat. A: Chem.* 2001, 173, 3; and G. A. Grasa, M. S. Viciu, J. Huang, C. Zhang, M. L. Trudell, S. P. Nolan, *Organomet.* 2002, 21, 2866.; and L. Yin, J. Liebscher, *Chem. Rev.* 2007, 107, 133.; and F. X. Felpin, T. Ayad, S. Mitra, *Eur. J. Org. Chem.* 2006, 2679; and C. Lui, F. Bao, Q. Ni, *Arkivoc xi*, 2011, 60.; and J. T. Guan, T. Q, Weng, G. Yu, S. H. Liu, *Tetrahedron Lett.* 2007, 48, 7129.; and A. Komaromi, Z. Novak, *Chem. Comm.* 2008, 4968.; and H. Huang, H. Liu, H. Jiang, K. Chen, *J. Org. Chem.* 2008, 73, 6037.; and Z. Gu, Z. Li, Z. Liu, Y. Wang, C. Liu, J. Xiang, *Catal. Comm,* 2008, 9, 2154.; and M. A. Casado, A. Fazal, L. A. Oro, *Arab. J. Sc. Eng.,* 2013, 38, 1631.; and G. K. Rao, A. Kumar, S. Kumar, U. B. Dupare, A. K. Singh, *Organometallics,* 2013, 32, 2452.; and T. W. Lyons, M. S. Sanford, *Chem. Rev.* 2010, 110, 1147.—each incorporated herein by reference in its entirety]. The products of these cross coupling reactions are extensively used in the production of important industrial raw materials, pharmaceutical and biologically active molecules [M. Toyota, C. Komori, M. J. Ihara, *Org. Chem.* 2000, 65, 7110.; and G. Amiet, H. M. Hugel, F. Nurlawis, *Synlett.* 2002, 3, 495.—each incorporated herein by reference in its entirety]. The ability of palladium complexes to function effectively as catalysts for cross coupling reactions has been attributed to the feasible and facile interchange between Pd(0) and Pd(II) or Pd(II) and Pd(IV). Plenty of homogeneous palladium complexes have been described to successfully catalyze various cross coupling reactions with high selectivity, high activity, and low catalyst loading. The complete removal of homogeneous catalysts from the cross coupling products is a complex and costly process, thus reducing the chances of industrial implementation since metal contamination in the end products is highly modulated by the pharmaceutical and related industries [V. Polshettiwar, C. Len, A. Fihri, *Coord. Chem. Rev.* 2009, 253, 2599.—incorporated herein by reference in its entirety].

A suitable method of overcoming the separation problem is immobilizing the homogeneous catalyst [H. Gruber-Woelfler, P. F. Radaschitz, P. W. Feenstra, W. Haas, J. G. Khinas, *J. Catal.* 2012, 286, 30.—incorporated herein by reference in its entirety]. Other than easy removal from the coupling products, the immobilized catalyst offers the potential of recycling and the possibility of for use in a continuous flow reactor [K. Hallamn, C. Moberg, *Tetrahedron: Asymmetry,* 2001, 12, 1475.—incorporated herein by reference in its entirety]. The ability to separate and reuse the supported catalyst makes it a more viable alternative, especially from an economical point of view. As a result of these substantial advantages, the interest in the use of immobilized palladium catalysts to catalyze cross coupling reactions has been increasing rapidly. Although several supported palladium catalysts have been reported, the application of supported palladium bis(oxazoline) complex catalysts in cross coupling reactions has not been widely explored.

In practice, the separation of the supported catalysts from the products is done either by decantation or by filtration. In these separation techniques, the recovery of all the catalyst is unlikely, and the decrease in reaction rate observed in the latter cycles of most supported catalytic systems is rarely due to catalyst deactivation, but rather is largely due to the inability to recover all of the catalyst during separation. Attempts have been made to simplify the recovery of the catalyst. These include, but are not limited to, applying biphasic reaction conditions, the use of sol gels, and membrane reactors [S. K. Karmee, C. Roosen, C. Kohlmann, S. Lutz, L. Greiner, W. Leitner, *Green Chem.* 2009, 11, 1052.; and F. Gelman, J. Blum, D. Avnir, *J. Am. Chem. Soc.* 2000, 122, 11999.; and L. Canatarella, A. Gallifuoco, A. Malandra, L. Martinkova, A. Spera, M. Cantarella, *Enzyme Microb. Technol.* 2011, 48, 345.—each incorporated herein by reference in its entirety].

Another way of aiding catalyst recovery is to contain the catalysts in a semipermeable membrane. The membrane that is required for this technique is designed to allow easy transportation of both reactants and products and have a pore size that guarantees retention of the catalyst. This design makes it possible to recover all of the catalyst after each catalytic run. The semipermeable membrane should also be compatible with all of the reaction conditions including the reactants, solvents, temperatures and pressures. The driving force in many of these reactions is usually temperature, pressure or concentration gradient [I. F. J. Vankelecom, *Chem. Rev.* 2002, 102, 3779.; and M. Gaab, S. Bellemin-Laponnaz, L. H. Gade, *Chem. Eur. J.* 2009, 15, 5450.—each incorporated herein by reference in its entirety].

In view of the forgoing, one object of the present disclosure is to provide a solid-supported catalyst ligand having suitable functionality for coordinating palladium (II) and a heterogeneous solid-supported palladium (II) catalyst thereof, such as a Merrifield resin supported palladium bis(oxazoline) catalyst. A further aim or the present disclosure is to provide methods for preparing the solid-supported catalyst ligand and solid-supported palladium (II) catalyst as well as methods employing the solid-supported catalyst in palladium cross-coupling reactions, such as, a Suzuki-Miyaura reaction, a Mizoroki-Heck reaction, and a Sonogashira reaction, demonstrating significant catalytic activity and recycling ability.

BRIEF SUMMARY OF THE INVENTION

According to a first aspect, the present disclosure relates to a solid-supported catalyst ligand of formula (I)

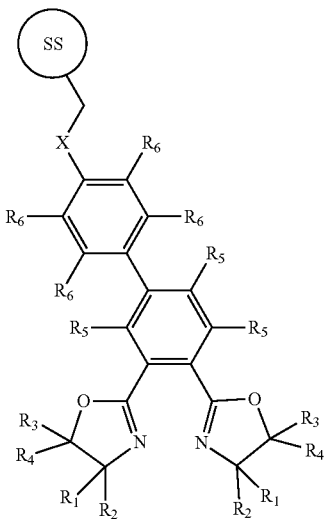

(I)

or a salt, solvate, tautomer or stereoisomer thereof; wherein i) $R_1$, $R_2$, $R_3$, and $R_4$ are independently —H, an optionally substituted alkyl, an optionally substituted cycloalkyl, or an optionally substituted aryl, ii) each $R_5$ and $R_6$ is independently —H, an optionally substituted alkyl, an optionally substituted cycloalkyl, or an optionally substituted aryl, iii) X is O, NH, or S, and iv) SS is a solid support with the proviso that the solid support is not silica.

In one embodiment, the solid support, SS, is Merrifield resin.

In one embodiment, $R_1$ is —$CH_3$, $R_2$ is —$CH_3$, $R_3$ is —H, $R_4$ is —H, $R_5$ is —H, $R_6$ is —H, and X is O and the solid-supported catalyst ligand of formula (I) is

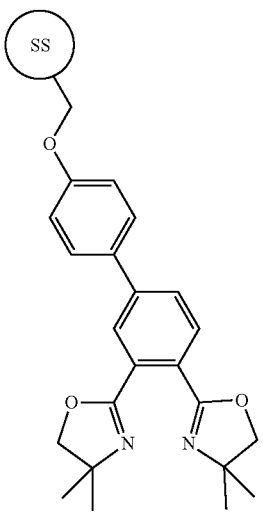

or a salt, solvate, tautomer or stereoisomer thereof wherein SS is a solid support with the proviso that the solid support is not silica.

In one embodiment, the solid support, SS, is Merrifield resin.

In one embodiment, the solid-supported catalyst the solid support, the solid-supported catalyst, or both is in the form of a particle having an average particle size in terms of an average diameter of 1-100 μm.

According to a second aspect, the present disclosure relates to a catalyst composition or solid-supported catalyst, comprising i) the solid-supported catalyst ligand and ii) a catalytic metal in the form of a $Pd^{2+}$ species having the formula $PdZ_2$, wherein the nitrogen atoms of the two oxazoline heterocycles chelate the catalytic metal and wherein Z is selected from the group consisting of —Cl, —I, —Br, —OAc, and —Otf.

In one embodiment, $R_1$ is —$CH_3$, $R_2$ is —$CH_3$, $R_3$ is —H, $R_4$ is —H, $R_5$ is —H, $R_6$ is —H, and X is O, the solid support, SS, is Merrifield resin, and the $Pd^{+2}$ species having the formula $PdZ_2$ is $PdCl_2$.

In one embodiment, the catalyst composition comprises 0.15-1.5 mmol of palladium per gram of the catalyst composition.

According to a third aspect, the present disclosure relates to a process for producing the solid-supported catalyst ligand, comprising i) reacting a phthalonitrile compound with halogen substitution at the 4-position with a 2-aminoalcohol in the presence of a Lewis acid catalyst to form a halogen substituted phenyl bisoxazoline ligand, ii) reacting the halogen substituted phenyl bisoxazoline ligand with a para-substituted phenylboronic acid compound in the presence of $Pd^{2+}$ and a first base to form a functionalized diphenyl bisoxazoline ligand, and iii) reacting the functionalized diphenyl bisoxazoline ligand with a second base in the presence of the solid support to form the solid-supported catalyst ligand, wherein the para-substituted phenylboronic acid has a para-substituent that is a hydroxyl, a thiol, or an amino group.

In one embodiment, the phthalonitrile compound is 4-iodophthalonitrile, the 2-aminoalcohol is 2-amino-2-methyl-1-propanol, the para-substituted phenylboronic acid compound is 4-hydroxy phenylboronic acid and the solid support is Merrifield resin.

In one embodiment, the Lewis acid catalyst is a metal triflate, the first base is an alkali carbonate, and the second base is an alkali hydride.

In one embodiment, the molar ratio of the 2-aminoalcohol to the phthalonitrile compound is in the range from 1:1 to 20:1.

According to a fourth aspect, the present disclosure relates to a method for a palladium cross-coupling reaction comprising reacting an aryl halide with a compound comprising a boronic acid, a terminal alkyne, or an alkene or derivatives thereof in the presence of a solvent, a base, and the catalyst composition to form a palladium cross-coupling product or derivatives thereof.

In one embodiment, $R_1$ is —$CH_3$, $R_2$ is —$CH_3$, $R_3$ is —H, $R_4$ is —H, $R_5$ is —H, $R_6$ is —H, and X is O, the solid support, SS, is Merrifield resin, and the $Pd^{+2}$ species having the formula $PdZ_2$ is $PdCl_2$.

In one embodiment, the method further comprises i) separating the catalyst composition from the palladium-cross coupling product or derivatives thereof to recover the catalyst composition and ii) reusing the catalyst composition in at least 2 reaction cycles with a less than 10% decrease in at least one selected from the group consisting of a turnover number and a turnover frequency.

In one embodiment, the molar yield of the palladium cross-coupling product or derivatives thereof is at least 75% relative to the initial molar amount of the aryl halide.

In one embodiment, the molar ratio of the aryl halide to the catalyst composition is greater than 100.

In one embodiment, the palladium cross-coupling product or derivatives thereof comprises less than 100 ppb palladium, based on the total weight of the palladium cross-coupling product or derivatives thereof.

In one embodiment, the catalyst composition is reused in at least 2 reaction cycles with a less than 20 percentage point decrease in a molar yield of the palladium cross-coupling product or derivatives thereof relative to an initial molar amount of the aryl halide The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
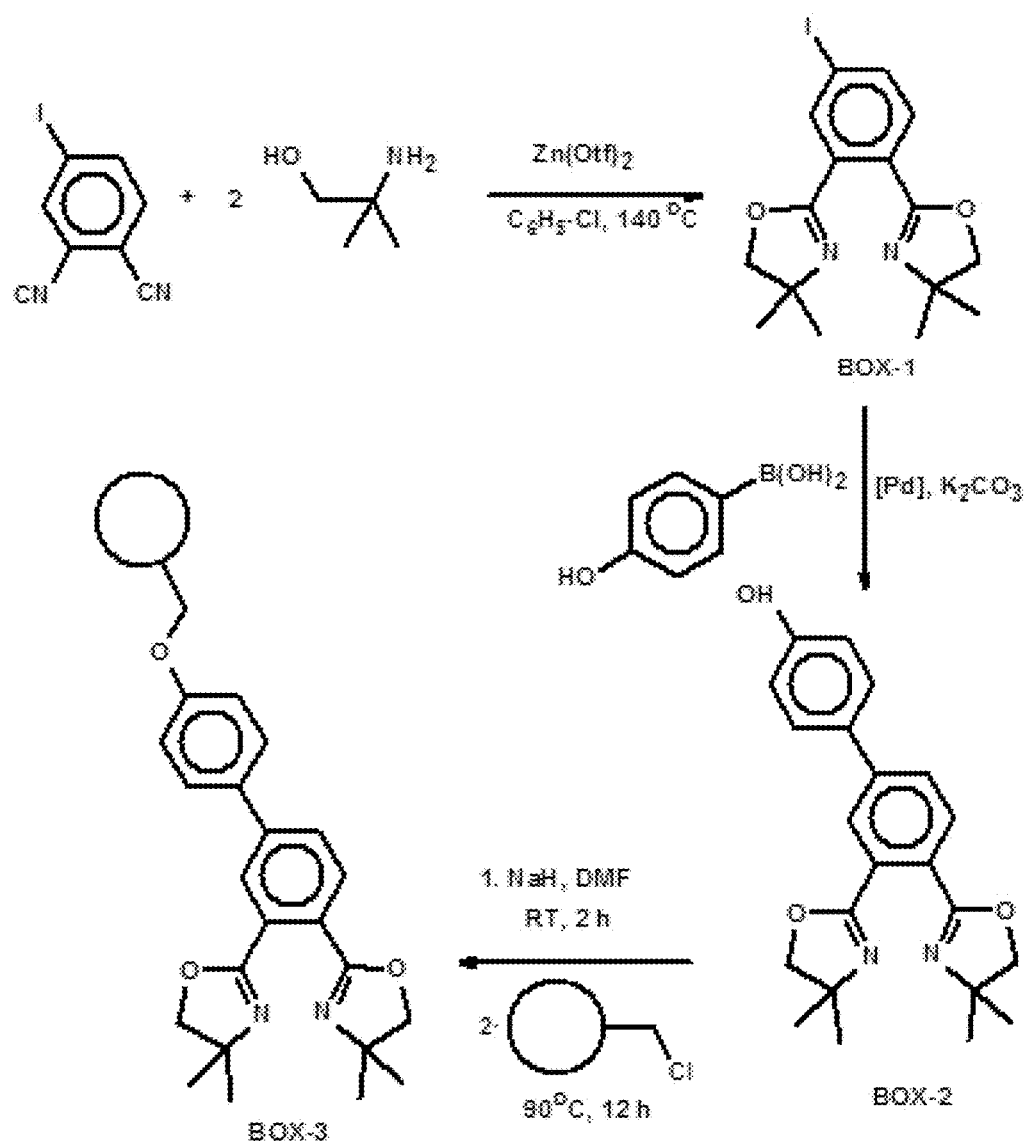
FIG. 1 is a chemical reaction scheme for the synthesis of the solid-supported catalyst ligand wherein $R_1$ is —$CH_3$, $R_2$ is —$CH_3$, $R_3$ is —H, $R_4$ is —H, $R_5$ is —H, $R_6$ is —H, and X is O, and the solid support, SS, is Merrifield resin (BOX-3) starting from 4-iodophthalonitrile and 2-amino-2-methyl-1-propanol.

Embodiments of the present disclosure will now be described more fully hereinafter with reference to the accompanying drawings, in which some, but not all of the embodiments of the present disclosure are shown.

The present disclosure will be better understood with reference to the following definitions.

As used herein, the words "a" and "an" and the like carry the meaning of "one or more".

As used herein, the terms "compound", "composition", "complex" and "catalyst" are used interchangeably, and are intended to refer to a chemical entity, whether in the solid, liquid or gaseous phase, as well as in a crude mixture or in a purified and isolated form. The chemical transformations and/or reactions described herein are envisaged to proceed via standard laboratory and experimental techniques in regard to performing the reaction as well as standard purification, isolation and characterization protocols known to those of ordinary skill in the art.

As used herein, the term "salt" refers to derivatives of the disclosed compounds wherein the parent compound is modified by making acid or base salts thereof. Exemplary salts include, but are not limited to, mineral or organic acid salts of basic groups such as amines, and alkali or organic salts of acidic groups such as carboxylic acids. The salts include, but are not limited to, the conventional non-toxic salts or the quaternary ammonium salts of the parent compound formed, for example, from non-toxic inorganic or organic acids. Exemplary conventional non-toxic salts include those derived from inorganic acids including, but not limited to, hydrochloric, hydrobromic, sulfuric, sulfamic, phosphoric, and nitric; and those derived from organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and mixtures thereof and the like. Further, salts of carboxylic acid containing compounds may include cations such as lithium, sodium, potassium, magnesium, and the like. The salts of the present disclosure can be synthesized from the parent compound that contains a basic or acidic moiety by conventional chemical methods. Generally such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvates include, but are not limited to, hydrates ethanolates, methanolates, isopropanolates and mixtures thereof. Methods of solvation are generally known to those of ordinary skill in the art.

As used herein, the term "tautomer" refers to constitutional isomers of organic compounds that readily convert by the chemical reaction of tautomerization or tautomerism. The reaction commonly results in the formal migration of a hydrogen atom or proton, accompanied by a switch of a single bond and adjacent double bond. Tautomerism is a special case of structural isomerism and because of the rapid interconversion; tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), enamine and enamine and anomers of reducing sugars.

Prototropy or prototropic tautomerism refers to the relocation of a proton. Prototropy may be considered a subset of acid base behavior. Prototropic tautomers are sets of isomeric protonation states with the same empirical formula and total charge. Tautomerizations may be catalyzed by bases (deprotonation, formation of an enolate or delocalized anion, and protonation at a different position of the anion) and/or acids (protonation, formation of a delocalized cation and deprotonation at a different position adjacent to the cation). Two additional subcategories of tautomerization include annular tautomerism, wherein a proton can occupy two or more positions of a heterocyclic system, and ring-chain tautomerism, wherein the movement of a proton is accompanied by a change from an open structure to a ring. Valence tautomerism is a type of tautomerism in which single and/or double bonds are rapidly formed and ruptured, without migration of atoms or groups. It is distinct from prototropic tautomerism, and involves processes with rapid reorganization of bonding electrons, such as open and closed forms of certain heterocycles, such as azide-tetrazole or mesoionic munchnone-acylamino ketene. Valence tautomerism requires a change in molecular geometry unlike canonical resonance structures or mesomers. In terms of the present disclosure, the tautomerism may refer to prototropic tautomerism, annular tautomerism, ring-chain tautomerism, valence tautomerism or mixtures thereof.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans-(E- and Z-) isomers, and non-enantiomeric optical isomers. Diastereomers seldom have the same physical properties. In terms of the present disclosure, stereoisomers may refer to enantiomers, diastereomers or both.

Conformers (rotamers), or conformational isomerism refers to a form of isomerism that describes the phenomenon of molecules with the same structural formula but with different shapes due to rotations about one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans-(or E- and Z-) stereoisomers of the compounds of the present disclosure wherein rotation about the double bond is restricted, keeping the substituents fixed relative to each other, are described and may be isolated as a mixture of isomers or as separated isomeric forms. S- and R-(or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example by chromatography, fractional crystallization, or use of a chiral agent.

As used herein, the term "substituted" refers to at least one hydrogen atom that is replaced with a non-hydrogen group, provided that normal valencies are maintained and that the substitution results in a stable compound. When a compound or substituent (—R group denoted as $R_1$, $R_2$, $R_3$ and so forth) is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidyl, pyrrolidinyl, piperidinyl, morpholinyl, piperazinyl, homopiperazinyl and the like), substituted heterocyclyl and mixtures thereof and the like. The substituted moiety may be either protected or unprotected as necessary, and as known to those skilled in the art.

As used herein, the term "alkyl" unless otherwise specified refers to both branched and straight chain saturated aliphatic primary, secondary, and/or tertiary hydrocarbons or hydrocarbon fragments of typically $C_1$ to $C_{10}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. As used herein, the term optionally includes substituted alkyl groups. Exemplary moieties with which the alkyl group can be substituted may be selected from the group including, but not limited to, hydroxyl, amino, alkylamino, arylamino, alkoxy, aryloxy, nitro, cyano, sulfonic acid, sulfate, phosphonic acid, phosphate, or phosphonate or mixtures thereof. The substituted moiety may be either protected or unprotected as necessary, and as known to those skilled in the art.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

As used herein, the term "aryl" unless otherwise specified refers to functional groups or substituents derived from an aromatic ring including, but not limited to, phenyl, biphenyl, napthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those skilled in the art.

As used herein, the term "heterocyclyl" unless otherwise specified refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has one or more oxygen atoms bonded to the ring (i.e. as ring atoms). Preferably, said atom which is bonded to the ring selected from nitrogen or sulphur. An example of a heterocyclyl substituted with one or more oxygen atoms is 1,1-dioxido-1,3-thiazolidinyl.

As used herein, "alkylthio" refers to a divalent sulfur with alkyl occupying one of the valencies and includes the groups methylthio, ethylthio, propylthio, butylthio, pentylthio, hexylthio, octylthio. As used herein, "alkanoyl" as used in this disclosure refers to an alkyl group having 2 to 18 carbon atoms that is bound with a double bond to an oxygen atom. Examples of alkanoyl includes, acetyl, propionyl, butyryl, isobutyryl, pivaloyl, valeryl, hexanoyl, octanoyl, lauroyl, stearoyl. As used herein, "arylalkyl" refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl. Examples of aroyl are benzoyl and naphthoyl, and "substituted aroyl" may refer to benzoyl or naphthoyl substituted by at least one substituent including those selected from halogen, amino, vitro, hydroxy, alkyl, alkoxy and haloalkyl on the benzene or naphthalene ring.

As used herein, "heteroarylcarbonyl" refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl. As used herein, vinyl refers to an unsaturated substituent having at least one unsaturated double bond and having the formula $CH_2$=CH—. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl.

As used herein, "hydrocarbyl" refers to a univalent hydrocarbon group containing up to about 24 carbon atoms (i.e., a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

As used herein, the term "solvent" refers to and includes, but is not limited to, water (e.g. tap water, distilled water, deionized water, deionized distilled water), organic solvents, such as ethers (e.g. diethyl ether, tetrahydrofuran, 1,4-dioxane, tetrahydropyran, t-butyl methyl ether, cyclopentyl methyl ether, di-iso-propyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, and mixtures of xylenes, toluene, mesitylene, anisole, 1,2-dimethoxybenzene, α,α,α,-trifluoromethylbenzene, fluorobenzene), chlorinated solvents (e.g. chlorobenzene, dichloromethane, 1,2-dichloroethane, 1,1-dichloroethane, chloroform), ester solvents (e.g. ethyl acetate, propyl acetate), amide solvents (e.g. dimethylformamide, dimethylacetamide, N-methyl-2-pyrrolidone), urea solvents, ketones (e.g. acetone, butanone), acetonitrile, propionitrile, butyronitrile, benzonitrile, dimethyl sulfoxide, ethylene carbonate, propylene carbonate, 1,3-dimethyl-3,4,5,6-tetrahydro-2(1H)-pyrimidinone, and mixtures thereof. As used herein solvent may refer to non-polar solvents (e.g. hexane, benzene, toluene, diethyl ether, chloroform, 1,4-dioxane), polar aprotic solvents (e.g. ethyl acetate, tetrahydrofuran, dichloromethane, acetone, acetonitrile, dimethylformamide, dimethyl sulfoxide) and polar protic solvents (e.g. acetic acid, n-butanol, isopropanol, n-propanol, ethanol, methanol, formic acid, water) and mixtures thereof.

As used herein, the term "base" refers to and includes, but is not limited to, an alkali metal hydride (e.g. sodium hydride, potassium hydride), an alkali metal hydroxide (e.g. lithium hydroxide, potassium hydroxide, sodium hydroxide, cesium hydroxide), an alkali metal carbonate (e.g. lithium carbonate, potassium carbonate, sodium carbonate, cesium carbonate), an alkali metal acetate (e.g. lithium acetate, sodium acetate, potassium acetate), an amine (e.g. a trialkylamine of formula NR'$_3$, wherein each R' may be independently ethyl, n-propyl, and n-butyl, a dialkylamine of formula HNR'$_2$, diethylamine, di-n-butylamine, pyrrolidine, piperidine, triethylamine, tri-n-butylamine, diisopropylethylamine, dicyclohexylmethylamine, pyridine, 2,6-dimethylpyridine, 4-aminopyridine, N-methyl-2,2,6,6-tetramethylpiperidine, 2,2,6,6-tetramethylpiperidine, 2,6-di-tert-butylpyridine, 1,4-diazabicyclo[2.2.2]octane, and mixtures thereof), and mixtures thereof. The presence of a base is often important for the palladium-catalyzed cross-coupling reactions in order to neutralize any hydrogen halide produced as a byproduct of the coupling reaction As used herein, the term "derivative" refers to a chemically modified version of a chemical compound that is structurally similar to a parent compound.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}$C and $^{14}$C. Isotopically labeled compounds of the invention can generally be prepared by conventional techniques known to those skilled in the art or by processes and methods analogous to those described herein, using an appropriate isotopically labeled reagent in place of the non-labeled reagent otherwise employed.

According to a first aspect, the present disclosure relates to a solid supported catalyst ligand of formula (I)

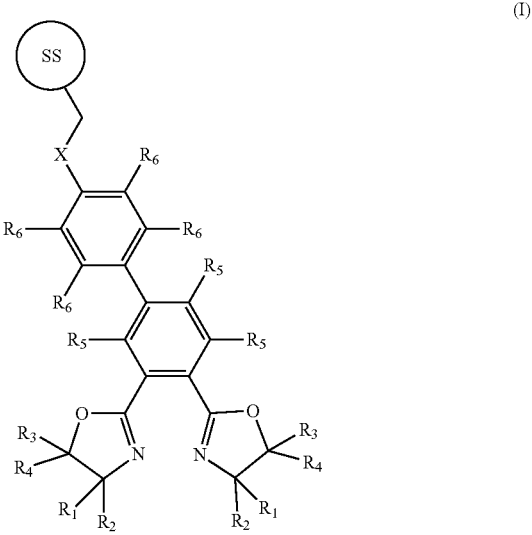

(I)

or a salt, solvate, tautomer or stereoisomer thereof wherein i) $R_1$, $R_2$, $R_3$ and $R_4$ are independently —H, an optionally substituted alkyl, an optionally substituted cycloalkyl, or an optionally substituted aryl, ii) each $R_5$ and $R_6$ is independently —H, an optionally substituted alkyl, an optionally substituted cycloalkyl, or an optionally substituted aryl, iii) X is O, NH, or S, and iv) SS is a solid support with the proviso that the solid support is not silica. In a preferred embodiment, the solid support is Merrifield resin.

Substituents $R_1$, $R_2$, $R_3$ and $R_4$ are independently —H, an optionally substituted alkyl, an optionally substituted cycloalkyl, or an optionally substituted aryl, preferably $R_1$ is —CH$_3$, $R_2$ is —CH$_3$, $R_3$ is —H, $R_4$ is —H and X is O. In certain embodiments, substituents $R_1$, $R_2$, $R_3$ and $R_4$ may be independently an optionally substituted cycloalkylalkyl, an optionally substituted arylalkyl, an optionally substituted heteroaryl, an optionally substituted heterocyclyl, an optionally substituted alkylthio, an optionally substituted alkanoyl, an optionally substituted aroyl, an optionally substituted heteroarylcarbonyl, an optionally substituted hydrocarbyl, an optionally substituted arylolefin, an optionally substituted arylalkylcarboxylic acid, or an optionally substituted vinyl.

Each $R_5$ and $R_6$ is independently —H, an optionally substituted alkyl, an optionally substituted cycloalkyl, or an optionally substituted aryl, preferably $R_5$ is —H, $R_6$ is —H, and X is O. In certain embodiments, each $R_5$ and $R_6$ substituent may be independently an optionally substituted cycloalkylalkyl, an optionally substituted arylalkyl, an optionally substituted heteroaryl, an optionally substituted heterocyclyl, an optionally substituted alkylthio, an optionally substituted alkanoyl, an optionally substituted aroyl, an optionally substituted heteroarylcarbonyl, an optionally substituted hydrocarbyl, an optionally substituted arylolefin, an optionally substituted arylalkylcarboxylic acid, or an optionally substituted vinyl.

The optionally substituted alkyl group may comprise 1-8 carbon atoms, preferably 1-5 carbon atoms, more preferably 1-3 carbon atoms. In one embodiment, the optionally substituted alkyl group comprises 1 carbon atom and is a methyl group. The optionally substituted aryl group is preferably a phenyl group. The alkyl and aryl groups may be substituted with the aforementioned substituents. Preferably, the alkyl and/or the aryl groups are substituted with hydroxyl, alkoxy, aryloxy, nitro, or cyano, either unprotected, or protected as necessary.

In certain embodiments, $R_1$, $R_2$, $R_3$, $R_4$, $R_5$, $R_6$, and $R_7$ may be independently a halogen atom, a hydroxyl, a nitro, a cyano, an optionally substituted heterocyclyl, an optionally substituted arylalkyl, an optionally substituted heteroaryl, or an optionally substituted alkoxyl. The optionally substituted heterocyclyl may be a derivative of an O-heterocyclyl such as tetrahydrofuran, tetrahydropyran, or dioxane. The optionally substituted heteroaryl may be a derivative of an O-heteroaromatic compound such as furan. The optionally substituted arylalkyl may be, but is not limited to, benzyl, phenethyl, and phenylpropyl. The optionally substituted alkoxyl may be, but is not limited to, methoxy, ethoxy, and phenoxyl.

In certain embodiments, $R_1$ and $R_2$ may not be an amino, an alkylamino, an arylamino, a N-monosubstituted amino, a N,N-disubstituted amino, a thiol or an optionally substituted thioalkoxyl because these groups contain nucleophilic atoms that may poison the catalyst. As used herein, the term "poisoning" refers to the nucleophilic atom(s) coordinating strongly to the palladium ion and thereby reducing the effectiveness of the catalyst.

As used herein, a solid support or catalyst support is a material, usually a solid with a high surface area, to which a catalyst or catalyst ligand is affixed. The activity of heterogeneous catalyst and nanomaterial-based catalysts occurs at the surface atoms. Consequently, great effort is made to maximize the surface area of a catalyst by distributing it over the support. The solid support may be inert or participate in the catalytic reactions, preferably it is inert. The recycling of homogeneous catalyst is complex and costly. Therefore, the use of immobilized catalyst is an alternative for industries to combine the advantages of both homogeneous and heterogeneous catalyst and also to overcome the problems related to metal contamination.

In certain embodiments, the solid support may be functionalized to facilitate a covalent attachment of the ligand. As used herein, the term "functionalize" refers to the modification of a surface of the solid support particle with an organic moiety containing carbon. Exemplary organic moieties include, without limitation, 4-benzyl chloride, 3-aminopropyl, 4-bromopropyl, 4-bromophenyl, 3-carboxypropyl, 2-(carbomethoxy)propyl, 3-chloropropyl, 3-(2-succinic anhydride)propyl, 1-(allyl)methyl, 3-(thiocyano)propyl, 3-(isocyano)propyl, propionyl chloride, 3-(maleimido) propyl, 3-(glycidoxy)propyl, 4-ethyl benzenesulfonyl chloride, 2-(3,4-epoxycyclohexyl)propyl, and 3-propylsulfonic acid, preferably 4-benzyl chloride. A loading of the organic moiety on the solid support may be in a range of 0.5-20 mmol/g, preferably 1-10 mmol/g, preferably 1-5 mmol/g, more preferably 1-3 mmol/g The nature of the solid support is not envisioned as particularly limiting. In certain embodiments, the catalyst is preferably immobilized by covalent coupling to a grafted or a functionalized polystyrene support. Exemplary functionalized polystyrene supports include, but are not limited to Wang resin, Argogel resin, Merrifield resin, Tentagel resin, Polyaamine resins, and the like, preferably Merrifield resin. In certain embodiments, the catalyst may be immobilized by covalent coupling to a grafted or a functionalized polymer support, wherein the functionalized polymer support is at least one selected from the group consisting of polyolefins, polyacrylates, polymethacrylates, and copolymers thereof.

In a most preferred embodiment, the solid support is Merrifield resin. As used herein, Merrifield resin refers to a cross-linked polystyrene resin that carries a chloromethyl functional group. Merrifield resin may be thought of as a polystyrene resin based on a copolymer of styrene and chloromethyl styrene. This polymer may further be cross-linked with divinyl benzene, wherein a degree of crosslinking is within the range of 1-5%, preferably 1-2%. In certain embodiments, the solid support comprises at least 10 wt % Merrifield resin relative to the total weight of the solid support, preferably at least 50 wt %, preferably at least 70 wt %, preferably at least 80 wt %, preferably at least 90 wt %, preferably at least 95 wt %, preferably at least 96 wt %, preferably at least 97 wt %, preferably at least 98 wt %, preferably at least 99 wt % Merrifield resin relative to the total weight of the solid support. It is equally envisioned that one or more solid supports may be used in addition to, or in lieu of Merrifield resin.

Alternatively, in certain embodiments, the catalyst may be immobilized by covalent coupling such as through a silicon or siloxane containing linker to a porous or nonporous solid support. Exemplary possible supports include, but are not limited to, alumina, titanium, kieselguhr, diatomaceous earth, clay, zeolites, carbon black, activated carbon, graphite, fluorinated carbon, organic polymers, metals, metal alloys, and mixtures thereof.

All embodiments carry the proviso that the solid support is not silica, particularly silica gel. As used herein "not silica" describes that the solid support comprises less than 25 wt % relative to the total weight of the solid support of a silica solid support, preferably less than 20 wt %, preferably less than 15 wt %, preferably less than 10 wt %, preferably less than 5 wt %, preferably less than 4 wt %, preferably less than 3 wt %, preferably less than 2 wt %, preferably less than 1 wt %, preferably less than 0.1 wt % based on the total weight of the solid support of a silica solid support. Exemplary silica solid supports include, but are not limited to, zeolite/aluminum silicate (e.g. andalusite, kyanite, sillimanite, kaolinite, metakalonite, 3:2 mullite, 2:1 mullite), amorphous silica, crystalline silica, fibrous silica, precipitated silica, mesoporous silica (e.g. MCM-41 and SBA-15), fumed silica, silica alumina, and silica gel, particularly silica gel.

The solid support, the solid-supported catalyst ligand or both may be in a form of a particle with a shape of a sphere, ellipsoid, cube, cuboid, cylindrical, or polygonal prism (e.g. triangular prism, hexagonal prism, and pentagonal prism). In a preferred embodiment, the solid support and/or solid-supported catalyst ligand particle has an irregular shape. An average diameter of the solid support and/or solid-supported catalyst ligand particle may be in a range of 1-100 µm, preferably 20-80 µm, more preferably 35-75 µm. In other embodiments, the average diameter of the solid support and/or solid-supported catalyst ligand particle is in a range of 0.5-1000 nm, preferably 1-500 nm, more preferably 5-100 nm. For spherical, ellipsoidal, or irregularly-shaped particles, the term "diameter" refers to a longest straight-line distance between two points on a surface of the particle.

In a preferred embodiment, a surface area of the solid support particle, the solid-supported catalyst ligand or both may range from 100-2000 $m^2/g$, preferably 300-1000 $m^2/g$, more preferably 500-1000 $m^2/g$. In certain embodiments, the solid support particle may comprise pores with an average diameter in a range of 0.5-50 nm, preferably 0.5-30 nm, more preferably 0.5-10 nm. In certain embodiments, a porosity of the solid support may be in a range of 1-99%, preferably 20-90%, more preferably 40-80%. In one embodiment, the solid support is non-porous. In a preferred embodiment, the catalyst ligand covers greater than 50% of the surface area of the solid support, preferably greater than 60%, preferably greater than 70%, preferably greater than 80%, preferably greater than 85%, preferably greater than 90%, preferably greater than 95% of the surface area of the solid support. In a preferred embodiment, the solid support is Merrifield resins and greater than 25% of the available chloromethyl substituents are bound to the catalyst ligand, preferably greater than 50%, preferably greater than 60%, preferably greater than 70%, preferably greater than 80%, preferably greater than 85%, preferably greater than 90%, preferably greater than 95% of the available chloromethyl substituents are bound to the catalyst ligand.

In a preferred embodiment, $R_1$ is —$CH_3$, $R_2$ is —$CH_3$, $R_3$ is —H, $R_4$ is —H, $R_5$ is —H, $R_6$ is —H, and X is O and the solid-supported catalyst ligand of formula (I) is compound BOX-3

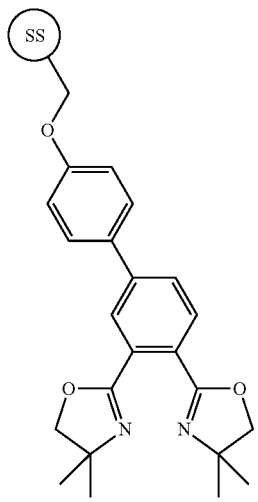

or a salt, solvate, tautomer or stereoisomer thereof wherein SS is a solid support with the proviso that the solid support, preferably Merrifield resin, is not silica. In a most preferred embodiment, $R_1$ is —$CH_3$, $R_2$ is —$CH_3$, $R_3$ is —H, $R_4$ is —H, $R_5$ is —H, $R_6$ is —H, and X is O, the solid-supported catalyst ligand of formula (I) is the compound BOX-3 as above and the solid support is Merrifield resin.

According to a second aspect, the present disclosure relates to a catalyst composition or solid-supported catalyst, comprising i) the solid-supported catalyst ligand of the first aspect and ii) a catalytic metal in the form of a $Pd^{2+}$ species or salt having the formula $PdZ_2$, wherein the nitrogen atoms of the two oxazoline heterocycles bind or chelate the catalytic palladium (II) metal and wherein Z is selected from the group consisting of —Cl, —I, —Br, —OAc, and —Otf. The terms "catalyst composition", "solid-supported palladium (II) complex" or "solid-supported catalyst" are used interchangeably. In a preferred embodiment, the catalyst composition or solid-supported catalyst is represented by a compound of formula (II)

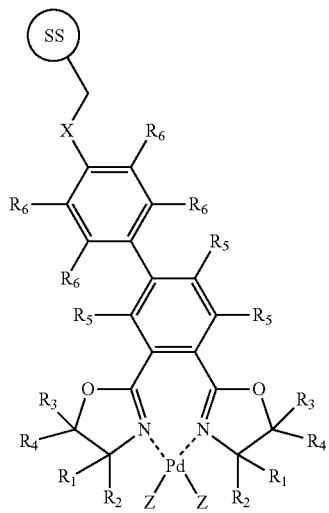

(II)

or a salt, solvate, tautomer or stereoisomer thereof, wherein $R_1$, $R_2$, $R_3$ and $R_4$ are independently —H, an optionally substituted alkyl, an optionally substituted cycloalkyl, or an optionally substituted aryl, each $R_5$ and $R_6$ is independently —H, an optionally substituted alkyl, an optionally substituted cycloalkyl, or an optionally substituted aryl, X is O, NH, or S, and SS is a solid support with the proviso that the solid support is not silica. In a most preferred embodiment, the solid support is Merrifield resin.

As used herein, a ligand refers to in coordination chemistry an ion or molecule (functional group) that binds a central metal atom to form a coordination complex. The binding between metal and ligand generally involves formal donation of one or more of the ligand's electron pairs. The nature of the metal-ligand bonding can range from covalent to ionic and the metal-ligand bond order can range from one to three. Ligands are classified in many ways including, but not limited to, size (bulk), the identity of the coordinating atom(s), and the number of electrons donated to the metal (i.e. denticity or hapticity). Denticity refers to the number of times a ligand bonds to a metal through noncontiguous donor sites. Many ligands are capable of binding metal ions through multiple sites, usually because the ligands have lone pairs on more than one atom. A ligand that binds through one site is classified as monodentate, a ligand that binds through two sites is classified as bidentate, three sites as tridentate and more than one site as polydentate. Ligands that bind via more than one atom are often termed chelating. Complexes of polydentate ligands are called chelate complexes. As used herein, chelation is a particular type of way ions and molecules bind to metal ions. It involves the formation or presence of two or more coordinate bonds between a polydentate (multiple bonded) ligand and a single central atom. These ligands are often organic compounds and may be referred to as chelants, chelators, chelating agents, or sequestering agents. The chelate effect describes the enhanced affinity of chelating ligands for a metal ion compared to the affinity of a collection of similar non-chelating (i.e. monodentate) ligands for the same metal. In terms of the present disclosure, the solid-supported catalyst ligand of the present disclosure may bind with one or more catalytic metal ions by monodentate coordination, or polydentate chelation including, but not limited to bidentate chelation or tridentate chelation to the metal ion, preferably Pd (II).

Herein, a ligand specifically may refer to an organic molecule comprising at least a phenyl ring and two oxazoline groups bound separately to the phenyl ring via a C—C bond and arranged ortho to one another, wherein each oxazoline group comprises a nitrogen atom which can bind to the palladium (II) ion covalently thereby forming a chelate. In a preferred embodiment, the nitrogen atoms of the two oxazoline heterocycles chelate the catalytic metal in a bidentate manner and the catalyst composition or solid-supported catalyst has a distorted square plane or square planar geometry. As used herein, square planar molecular geometry describes the stereochemistry (spatial arrangement) of atoms that is adopted by certain chemical compounds wherein molecules of this geometry have their atoms (i.e. oxazoline —N) positioned at the corners of a square on the same plane about a central atom (i.e. $Pd^{2+}$).

As used herein, the term catalytic metal in the form of a $Pd^{+2}$ species or palladium (II) salt having the formula $PdZ_2$ includes, but is not limited to, palladium (II) chloride, palladium (II) bromide, palladium (II) iodide, bis(benzonitrile) palladium (II) chloride, bis(acetonitrile) palladium (II) chloride, palladium (II) acetate, palladium (II) triflate, and the like. It is equally envisioned that the solid supported catalytic ligand of the present disclosure may be adapted to or in its present form bind one or more additional catalytic metals. Exemplary additional catalytic metals that may be bound in addition to or in lieu of Pd (II) include, but are not limited to nickel, platinum, rhodium, iron, gold, silver, ruthenium, and iridium.

In a preferred embodiment, $R_1$ is —$CH_3$, $R_2$ is —$CH_3$, $R_3$ is —H, $R_4$ is —H, $R_5$ is —H, $R_6$ is —H, and X is O, and the $Pd^{12}$ species having the formula $PdZ_2$ is $PdCl_2$ and the catalyst composition or solid-supported catalyst according to formula (II) is

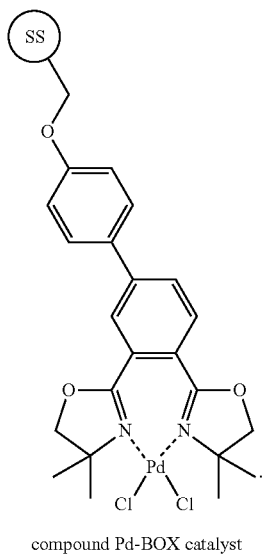

compound Pd-BOX catalyst or a salt, solvate, tautomer or stereoisomer thereof wherein SS is a solid support with the proviso that the solid support, preferably Merrifield resin, is not silica. In a most preferred embodiment, $R_1$ is —$CH_3$, $R_2$ is —$CH_3$, $R_3$ is —H, $R_4$ is —H, $R_5$ is —H, $R_6$ is —H, and X is O, the solid-supported catalyst ligand of formula (I) is the compound Pd-BOX as above and the solid support is Merrifield resin.

In a preferred embodiment, the solid-supported catalyst or catalyst composition comprises 0.05-1.5 mmol of palladium per gram of solid-supported catalyst, preferably 0.1-1.0 mmol/g, preferably 0.2-0.9 mmol/g, preferably 0.3-0.8 mmol/g, preferably 0.4-0.7 mmol/g, preferably 0.45-0.65 mmol/g, preferably 0.5-0.6 mmol of palladium per gram of solid-supported catalyst. In certain embodiments, the amount of palladium loading in the solid-supported catalyst or catalyst composition may be determined by elemental analysis and/or inductively coupled plasma mass spectroscopy (ICP-MS). In a preferred embodiment, the solid-supported catalyst or catalyst composition has a turnover number in the range of 1500-2500, preferably 1500-2000, preferably 1700-2000. In a preferred embodiment, the solid-supported catalyst or catalyst composition has a turnover frequency in the range of 200-1500 cycle per hour, preferably 200-1000 cycles per hour, more preferably 200-500 cycles per hour. In certain embodiments, the aforementioned values of turnover number and turnover frequency of the solid-supported catalyst or catalyst composition may be observed when the catalyst catalyzes any palladium catalyzed reaction, preferably any palladium cross-coupling reaction. Exemplary palladium cross-coupling reactions include, but are not limited to, Mizoroki-Heck reaction, Mizoroki-Heck-Matsuda reaction, Sonagashira reaction, Kumada reaction, Negishi reaction, Stille reaction, Suzuki reaction, Suzuki-Miyaura reaction, Hiyama reaction, Buchwald-Hartwig reaction, and the like.

According to a third aspect, the present disclosure relates to a process for producing the solid-supported catalyst ligand, comprising i) reacting a phthalonitrile compound with halogen substitution at the 4-position (i.e. 4-halopthalonitrile) with a 2-aminoalcohol (i.e. β-amino alcohol) in the presence of a Lewis acid catalyst to form a halogen substituted phenyl bisoxazoline ligand, ii) reacting the halogen substituted phenyl bisoxazoline ligand with a para-substituted phenylboronic acid compound in the presence of $Pd^{2+}$ and a first base to form a functionalized diphenyl bisoxazoline ligand, and iii) reacting the functionalized diphenyl bisoxazoline ligand with a second base in the presence of the solid support to form the solid-supported catalyst ligand, wherein the para-substituted phenylboronic acid has a para-substituent that is a hydroxyl, a thiol, or an amino group.

In one step of the 4-halopthalonitrile compound is reacted with a 2-aminoalcohol in the presence of a Lewis acid catalyst to form a halogen substituted phenyl bisoxazoline ligand. In a preferred embodiment, the 4-halopthalonitrile compound is a compound of formula (III)

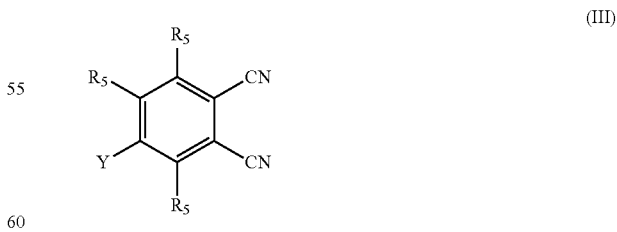

or a salt, solvate, tautomer or stereoisomer thereof, wherein each $R_5$ is independently —H, an optionally substituted alkyl, an optionally substituted cycloalkyl, or an optionally substituted aryl and Y is —I, —Br, or —Cl, preferably each $R_5$ is —H and Y is —I. In a preferred embodiment the compound of formula (III) is

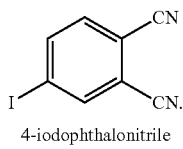

4-iodophthalonitrile

In a preferred embodiment, the 2-aminoalcohol is a compound of formula (IV)

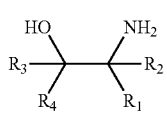
(IV)

or a salt, solvate, tautomer or stereoisomer thereof, wherein $R_1$, $R_2$, $R_3$, and $R_4$ are independently —H, an optionally substituted alkyl, an optionally substituted cycloalkyl, or an optionally substituted aryl, preferably $R_1$ and $R_2$ are —CH$_3$, and $R_3$ and $R_4$ are –H. In a preferred embodiment the compound of formula (IV) is

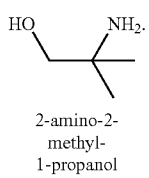

2-amino-2-methyl-1-propanol

As used herein, a Lewis acid catalyst or Lewis acid catalysis refers to organic reactions wherein a metal-based Lewis acid acts as an electron pair acceptor to increase the reactivity of a substrate. Common Lewis acid catalyst are based on main group metals including, but not limited to, aluminum, boron, silicon, and tin, as well as many early (i.e. titanium, zirconium) and late (i.e. iron, copper, zinc) d-block metals. Generally, the metal atom forms an adduct with a lone-pair bearing electronegative atom in the substrate such as oxygen (both sp$^2$ or sp$^3$), nitrogen, sulfur, and/or halogens. The complexation generally has partial charge-transfer character and makes the lone-pair donor effectively more electronegative, activating the substrate toward nucleophilic attack, heterocyclic bond cleavage, or cycloaddition. Many reaction involving carbon-carbon or carbon-heteroatom bond formation can be catalyzed by Lewis acids. Exemplary Lewis acid catalysts or reagents include, but are not limited to, TiC$_4$, BF$_3$, SnCl$_4$, AlCl$_3$ and the like. In a preferred embodiment, the Lewis acid catalyst is a triflate or triflate salt, preferably a transition metal triflate salt, most preferably zinc triflate (Zn(OTf)$_2$). In certain embodiments, other triflate salts such as lanthanide triflates of the formula Ln(OTf)$_3$ (where Ln=La, Ce, Pr, Nd, Sm, Eu, Gd, Tb, Dy, Ho, Er, Tm, Yb, Lu, Y) and scandium triflate are used.

In a preferred embodiment, the 4-halophthalonitrile, preferably 4-iodophthalonitrile, and the Lewis acid catalyst, preferably a triflate or triflate salt, most preferably zinc triflate (Zn(OTf)$_2$) in a dried organic solvent, preferably chlorobenzene are stirred at room temperature for approximately 15 minutes. An amount of 4-halophthalonitrile in a range of 1-20 mmol, preferably 1-10 mmol, more preferably 1-5 mmol and an amount of the Lewis acid triflate salt is in a range of 0.1-1 mmol, preferably 0.1-0.5 mmol, more preferably 0.1-0.3 mmol, and 1-10 mol % relative to the number of moles of the 4-halophthalonitrile, preferably 1-8 mol %, more preferably 3-6 mol %. Exemplary organic solvents include, but are not limited to, benzene, toluene, p-xylene, o-xylene, and m-xylene. An amount of the organic solvent is in a range of 5-50 ml, preferably 10-40 ml, more preferably 20-40 ml. The solution may be stirred for 5-60 minutes, preferably 5-30 minutes, more preferably 10-20 minutes at a temperature in a range of 10-40° C., preferably 15-30° C., more preferably 20-30° C.

A solution of the 2-aminoalcohol of n-amino alcohol of the following structure, preferably 2-amino-2-methyl-1-propanol in dried chlorobenzene may be added to the solution of 4-halophthalonitrile and triflate salt in dried chlorobenzene to form a reaction mixture. An amount of the β-amino alcohol is in a range of 1-40 mmol, preferably 1-30 mmol, more preferably 1-15 mmol, and a molar ratio of 2-amino-1-propanol to 4-halophthalonitrile is in a range of 1:1 to 20:1, preferably 1:1 to 10:1, more preferably 1:1 to 5:1. The 2-aminoalcohol may be further substituted and comprise the aforementioned substituents on C-1, C-2, or both, and may be a chiral reagent, an achiral reagent, or a racemic mixture. Preferably, an achiral 2-amino-2-methyl-1-propanol is used. In other embodiments, a chiral ligand is prepared by employing only one of the enantiomers of 2-amino-1-propanol (or further substituted 2-amino-1-propanol), such as (S)-(+)-2-amino-1-propanol or (R)-(−)-2-amino-1-propanol.

The temperature of the reaction mixture may be raised to 80-160° C., preferably 100-160° C., more preferably 110-140° C. and may be refluxed for 12-48 hours, preferably 18-48 hours, more preferably 18-36 hours. The precursor, the halogen substituted phenyl bisoxazoline ligand, may be isolated and purified by methods known to those skilled in the art, such as filtration through a celite containing cartridge, aqueous work-up, extraction with organic solvents, distillation, crystallization, column chromatography, and high pressure liquid chromatography (HPLC) on normal phase or reversed phase. Preferred methods include, extraction with organic solvents and column chromatography, but are not limited to those exemplified. The yield of the precursor, the halogen substituted phenyl bisoxazoline ligand is at least 50%, preferably at least 75%, more preferably at least 80%.

In another step, the precursor, halogen substituted phenyl bisoxazoline ligand reacts with a para-substituted phenylboronic acid compound, arylboronic acid, or equally envisaged arylboronic ester in the presence of Pd$^{2+}$ and a first base to form a functionalized diphenyl bisoxazoline ligand. In a preferred embodiment, the precursor, halogen substituted phenyl bisoxazoline ligand is a compound of formula V

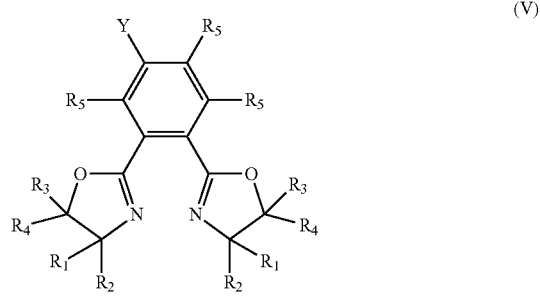
(V)

or a salt, solvate, tautomer or stereoisomer thereof, wherein each $R_5$ is independently —H, an optionally substituted alkyl, an optionally substituted cycloalkyl, or an optionally substituted aryl and Y is —I, —Br, or —Cl, preferably each $R_5$ is —H and Y is —I. In a preferred embodiment the compound of formula (V) is

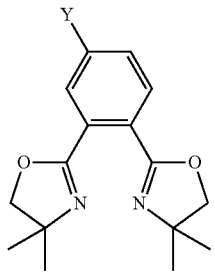

2,2'-(4-Iodobenzene-1,2-diyl)bis(4,4-dimethyl-4,5-dihydro-1,3-oxazole) or the bis(oxazoline) precursor ligand (BOX-1).

In a preferred embodiment, the para-substituted phenylboronic acid is a compound of formula (VI)

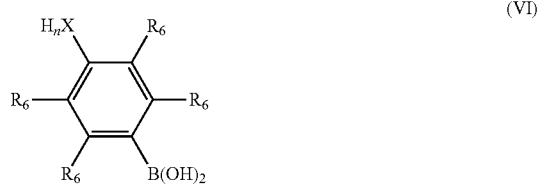

(VI)

or a salt, solvate, tautomer or stereoisomer thereof, wherein each $R_6$ is independently —H, an optionally substituted alkyl, an optionally substituted cycloalkyl, or an optionally substituted aryl and n is 1 with the proviso that X is O or S or n is 2 with the proviso that X is N, preferably each $R_6$ is —H, n is 1, and X is O. In a preferred embodiment the compound of formula (VI) is

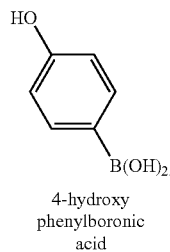

4-hydroxy phenylboronic acid

In a preferred embodiment, the precursor halogen substituted phenyl bisoxazoline ligand, a palladium(II) salt or $Pd^{+2}$ source, a first base, and an arylboronic acid or an arylboronic ester, preferably an para-substituted phenylboronic acid may be added to a solvent and heated to a temperature in a range of 50-150° C., preferably 60-100° C., more preferably 60-80° C. for 1-48 hours, preferably 1-24 hours, more preferably 1-10 hours. Preferably, the palladium(II) salt or $Pd^{+2}$ source is palladium(II) chloride, the base is an alkali carbonate, preferably potassium carbonate, and the solvent may comprise water, alcohol, toluene, dimethyl formamide, tetrahydrofuran, acetone, or mixtures thereof. Preferably, the solvent is a mixture consisting of dimethyl formamide and water and comprises 10-50 vol %, preferably 30-50 vol %, more preferably 40-50 vol % of water, based on a total volume of the solvent. A volume of the solvent may be in a range of 1-20 ml, preferably 1-10 ml, more preferably 1-5 ml.

In a preferred embodiment, the arylboronic acid/ester comprises a hydroxy, amine, or a thiol substituent and may be further substituted with the aforementioned substituents (e.g. $R_6$). Preferably, the arylboronic acid/ester is preferably a para-substituted phenylboronic acid, most preferably 4-hydroxy phenylboronic acid. An amount of the precursor halogen substituted phenyl bisoxazoline ligand may be in a range of 0.1-10 mmol, preferably 0.1-3 mmol, more preferably 0.1-1 mmol. An amount of the palladium(II) salt or $Pd^{+2}$ source may be in a range of 1-20 mol %, preferably 1-10 mol %, more preferably 4-6 mol %, based on the number of moles of the precursor halogen substituted phenyl bisoxazoline ligand. An amount of the base, preferably potassium carbonate may be in a range of 1-10 molar equivalents, more preferably 1-5 molar equivalents, more preferably 1-3 molar equivalents of the amount of the precursor halogen substituted phenyl bisoxazoline ligand. An amount of the arylboronic acid/ester may be in a range of 1-10 molar equivalents, more preferably 1-2 molar equivalents, more preferably 1-1.5 molar equivalents of the amount of the precursor halogen substituted phenyl bisoxazoline ligand. The ligand may be isolated and purified by methods known to those skilled in the art, such as filtration through a celite containing cartridge, aqueous work-up, extraction with organic solvents, distillation, crystallization, column chromatography, and high pressure liquid chromatography (HPLC) on normal phase or reversed phase. The yield of the functionalized diphenyl bisoxazoline ligand is at least 50%, preferably at least 75%, more preferably at least 80%.

In another step, the functionalized diphenyl bisoxazoline ligand reacts with a second base in the presence of the solid support to form the solid-supported catalyst ligand. In a preferred embodiment, the functionalized diphenyl bisoxazoline ligand is a compound of formula (VII)

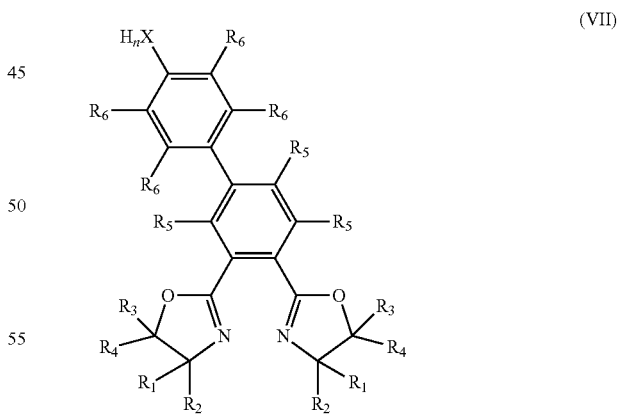

(VII)

or a salt, solvate, tautomer or stereoisomer thereof wherein $R_1$, $R_2$, $R_3$ and $R_4$ are independently —H, an optionally substituted alkyl, an optionally substituted cycloalkyl, or an optionally substituted aryl, each $R_5$ and $R_6$ is independently —H, an optionally substituted alkyl, an optionally substituted cycloalkyl, or an optionally substituted aryl, n is 1 with the proviso that X is O or S or n is 2 with the proviso that X is N, preferably $R_1$ is —CH$_3$, $R_2$ is —CH$_3$, $R_3$ is —H, $R_4$ is —H, R₅ is —H, R₆ is —H, n is 1, and X is O and the functionalized diphenyl bisoxazoline ligand of formula (VII) is

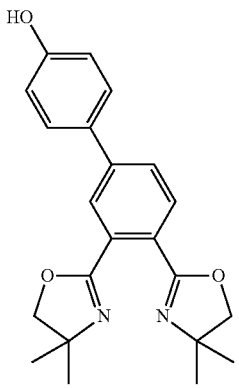 [SMILES: CC1(C)COC(c2ccc(-c3ccc(O)cc3)cc2C2=NC(C)(C)CO2)=N1]

3,4'-Bis(4,4-dimethyl-4,5-dihydro-1,3-oxazole-2-yl)biphenyl-4-ol or the functionalized diphenyl bis(oxazoline) precursor ligand (BOX-2).

A second base, preferably a an alkali hydride, preferably sodium hydride may be added to a solution of the functionalized diphenyl bisoxazoline ligand in a dry organic solvent to form a mixture which is stirred for 1-10 hours, preferably 1-5 hours, more preferably 1-3 hours at a temperature in a range of 15-50° C., preferably 20-40° C., more preferably 20-30° C. under an inert atmosphere provided by nitrogen gas, helium gas, argon gas, or mixtures thereof. An amount of the functionalized diphenyl bisoxazoline ligand may range from 0.1-5 mmol, preferably 0.1-1 mmol, more preferably 0.1-0.5 mmol. An amount of the second base, preferably an alkali hydride, may be in a range of 1-10 molar equivalents, more preferably 1-5 molar equivalents, more preferably 1-2 molar equivalents of the amount of the functionalized diphenyl bisoxazoline ligand. Preferably, the second base is sodium hydride. The solid support particle is then added to the mixture and then stirred at a temperature in a range of 40-150° C., preferably 40-100° C., more preferably 80-100° C. for 1-96 hours, preferably 1-48 hours, more preferably 10-20 hours. The solid-supported catalyst ligand of formula (I) may be isolated and purified by methods known to those skilled in the art, such as filtration through a celite containing cartridge. The solid-supported catalyst ligand may also be washed with solvents, such as methanol, water, acetone, and dichloromethane, and dried under reduced pressure (e.g. 0.1-50 mbar, preferably 0.1-10 mbar, more preferably 0.1-1 mbar). The yield of the solid-supported catalyst ligand is at least 70%, preferably at least 80%, more preferably at least 90%.

In a preferred embodiment, the method may further comprise stirring the solid-supported catalyst ligand of formula (I) in the presence of a palladium (II) salt to form the catalyst composition, solid-supported palladium (11) complex, or solid supported catalyst of formula (II). The solid-supported catalyst ligand of formula (I) may be suspended and stirred in a dry organic solvent (e.g. toluene, benzene, dimethyl sulfoxide, tetrahydrofuran, or mixtures thereof) for 5-120 minutes, preferably 5-90 minutes, more preferably 10-60 minutes. An amount of the solid-supported catalyst ligand is in a range of 0.1-5 mmol, preferably 0.1-3 mmol, more preferably 0.1-1 mmol. A solution of a palladium (II) salt, as described herein and previously described, preferably bis(benzonitrile) palladium (II) chloride, in the same solvent is added to the solid-supported catalyst ligand and the resulting mixture may be stirred at a temperature in a range of 40-150° C., preferably 40-100° C., more preferably 80-100° C. for 1-96 hours, preferably 1-48 hours, more preferably 10-20 hours. A molar ratio of the solid-supported catalyst ligand to the palladium (II) salt is in a range of 1:1 to 1:2, preferably 1:1 to 2:3, more preferably 1:1 to 1:1.2. The solid-supported catalyst or catalyst composition may also be washed with solvents, such as ethanol, methanol, water, acetone, and dichloromethane, and dried under reduced pressure (e.g. 0.1-50 mbar, preferably 0.1-10 mbar, more preferably 0.1-1 mbar). The yield of the solid-supported catalyst or catalyst composition is at least 70%, preferably at least 80%, more preferably at least 90%, most preferably at least 95%.

According to a fourth aspect, the present disclosure relates to a method for a palladium cross-coupling reaction comprising reacting an aryl halide with a compound comprising a boronic acid, a terminal alkyne, or an alkene or derivatives thereof in the presence of a solvent, a base, and the catalyst composition to form a palladium cross-coupling product or derivatives thereof.

As used herein, a palladium cross-coupling reaction or palladium-catalyzed coupling reactions comprises a family of cross-coupling reactions that employ palladium complexes as catalysts. The reactions generally obey the stoichiometry of formula (VIII)

$$X—R+M-R''\rightarrow MX+R—R'' \qquad (VIII)$$

Exemplary palladium cross-coupling reactions include, but are not limited to, a Neigishi coupling between an organohalide and an organozinc compound, a Heck reaction between alkenes and aryl halides, a Suzuki reaction between aryl halides and boronic acids, a Stille reaction between organohalides and organotin compounds, a Hiyama coupling between organohalides and organosilicon compounds, a Sonogashira coupling between aryl halides and alkynes, optionally with copper(I) iodide as a co-catalyst, a Buchwald-Hartwig amination of an aryl halide with an amine, optionally extended to aryl halide with phenol and thiol, a Kumada coupling of grignards and aryl or vinyl halides, a Heck-Matsuda reaction of an arenediazonium salt with an alkene, and the like.

In a preferred embodiment, the palladium cross-coupling reaction is at least one selected from the group consisting of a Suzuki-Miyaura reaction, a Mizoroki-Heck reaction, and a Sonagashira reaction. As used herein, the Suzuki-Miyaura, or the Suzuki reaction is an organic reaction classified as a coupling reaction between a boronic acid and an organohalide catalyzed by a palladium complex. It is widely used to synthesize palladium cross-coupling products including, but not limited to poly-olefins, styrene, and substituted biphenyls. Generally, a carbon-carbon single bond is formed by coupling an organoboron species with a halide using a palladium catalyst and a base. As used herein, the Mizoroki-Heck, or Heck reaction is the chemical reaction of an unsaturated halide, or triflate, with an alkene in the presence of a base and a palladium catalyst to form a substituted alkene. As used herein, the Sonagashira reaction is a cross-coupling reaction employing a palladium catalyst to form a carbon-carbon bond between a terminal alkyne and aryl or vinyl halide.

As used herein, the aryl halide comprises an optionally substituted aryl group which may comprise the aforementioned substituents. Preferably, the aryl group is phenyl. In a preferred embodiment, the substituents are electron-donating groups such as amino, alkoxyl, and alkyl. In another preferred embodiment, the substituents are electron-withdrawing groups such as nitro, cyano, and acetyl. The aryl group may comprise up to 5 substituents. Preferably, there is one substituent. The substituent may be located ortho, meta, or para to the halogen atom. Preferably, the substituent is located para to the halogen atom. The aryl halide may be an aryl monohalide such as aryl chloride, aryl bromide, and aryl iodide. Preferably, the aryl monohalide is an aryl iodide such as iodobenzene. Exemplary aryl monohalide includes, without limitation, iodobenzene, 4-iodoaniline, 4-iodoacetophenone, 4-iodobenzonitrile, 4-iodoanisole, bromobenzene, 4-bromoacetophenone, and 1-iodo-4-nitrobenzene. In another embodiment, the aryl halide is an aryl dihalide such as 1,4-dichlorobenzene, 1,4-dibromobenzene, and 1,4-diiodobenzene. Preferably, the aryl halide is 1,4-diiodobenzene. It is equally envisaged that other organohalides, vinyl halides, triflates (e.g. aryl triflate, benzyl triflate, or vinyl triflate), or tosylates (aryl tosylate, benzyl tosylate, or vinyl tosylate) may be employed.

In a preferred embodiment, the aryl halide is at least one selected from the group consisting of iodobenzene, bromobenzene, chlorobenzene, 1-iodo-4-nitrobenzene, 1-bromo-4-nitrobenzene, 1-chloro-4-nitrobenzene, 1-iodo-4-methoxybenzene, 1-bromo-4-methoxybenzene, 1-chloro-4-methoxybenzene, 1-iodo-4-methylbenzene, 1-bromo-4-methylbenzene, 1-chloro-4-methylbenzene, 4-iodobenzoic acid, 4-bromobenzoic acid, 4-chlorobenzoic acid, 4-iodoacetophenone, 4-bromoacetophenone, 4-chloroacetophenone, 4-iodoaniline, 4-bromoaniline, and 4-chloroaniline.

As used herein, a boronic acid is an alkyl or aryl substituted boric acid containing a carbon-boron bond belonging to the larger class or organoboranes. Exemplary boronic acids include, but are not limited to, phenylboronic acid, 2-thienylboronic acid, methyl boronic acid, cis-propenylboronic acid, trans-propenyl boronic acid and the like. It is equally envisaged that boronic esters and other organoborane species may be employed. As used herein, terminal alkynes have the formula $RC_2H$ and examples include methylacetylene and acetylene. As used herein, an alkene is an unsaturated hydrocarbon that contains at least one carbon-carbon double bond. The boronic acid, the terminal alkyne, and the alkene may be optionally substituted which may comprise the aforementioned substituents.

Preferably, the solid-supported catalyst system tolerates a variety of functional groups on the halide and/or the boronic acid/terminal alkyne/alkene and derivatives thereof. That is, the solid-supported catalyst retains the aforementioned turnover number and turnover frequency regardless of the functional groups on the halides and/or the boronic acid/terminal alkyne/alkene In certain embodiments, prior to the reacting, the method further comprises an adding step wherein the solid-supported catalyst or catalyst composition is added to the organic solvent, followed by the reactants, the base, and water to form a reaction mixture. In another embodiment, the base is first dissolved in water to form a basic solution, which is then added to the other compounds in the organic solvent. In one embodiment, the solid-supported catalyst is not preformed but is formed in situ in a reaction flask (i.e. at least one of the aforementioned palladium (II) salts and the solid-supported catalyst ligand of formula (I) are added to the reaction flask separately). Preferably, the adding step is performed in air. In another embodiment, the adding step is performed in an inert atmosphere provided by an inert gas such as argon, nitrogen, helium, or mixtures thereof.

In a preferred embodiment, the solvent may comprise 5-95% by volume of water and 5-95% by volume of an organic solvent, based on a total volume of the solvent. Preferably, the solvent comprises 30-70% by volume of water and 30-70% by volume of an organic solvent, based on the total volume of the solvent. Most preferably, the solvent consists of 50% by volume of water and 50% by volume of the organic solvent, based on the total volume of the solvent. Preferably, deionized distilled water is used. Preferably, the organic solvent is a polar aprotic solvent, more preferably dimethylformamide or acetonitrile.

In a preferred embodiment, the aryl halide or vinyl halide is the limiting reagent in the palladium cross-coupling reaction. An amount of the aryl halide may be in a range of 0.5-20 mmol, preferably 0.5-10 mmol, more preferably 0.5-5 mmol. An amount of the boronic acid, terminal alkyne or alkene or derivatives thereof may be in a range of 0.5-100 mmol, preferably 0.5-50 mmol, more preferably 0.5-25 mmol, or 1-5 molar equivalents, preferably 1-3 molar equivalents, more preferably 1-2 molar equivalents of the amount of aryl halide or vinyl halide. An amount of the base may be in a range of 0.5-100 mmol, preferably 0.5-50 mmol, more preferably 1-25 mmol, or 1-5 molar equivalents, preferably 1-3 molar equivalents, more preferably 2-3 molar equivalents of the amount of aryl halide or vinyl halide.

In a preferred embodiment, an amount of the solid-supported catalyst may range from 0.001-10 mol % of a number of moles of the aryl halide or vinyl halide, more preferably 0.005-5 mol %, more preferably 0.01-2 mol %, more preferably 0.1-1.0 mol %, although higher catalyst loadings (e.g. up to 20 mol %, 30 mol %, 40 mol %, 80 mol %) may be used and the method will still proceed as intended. In a preferred embodiment, the molar ratio of the aryl halide or vinyl halide to the catalyst composition or solid-supported catalyst is greater than 100, preferably greater than 200, preferably greater than 400, preferably greater than 500.

In a preferred embodiment, the reacting may be performed at a temperature in a range of 35-110° C., preferably 50-110° C., more preferably 70-100° C. An external heat source, such as a water bath or an oil bath, an oven, microwave, or a heating mantle, may be employed to heat the reaction mixture. In a preferred embodiment, the external heat source is a thermostatted thermocirculator. In one embodiment, the aqueous solution is not heated with microwave irradiation. Preferably, the reacting is performed in air. In another embodiment, the reacting is performed in an inert atmosphere provided by the aforementioned inert gases.

In a preferred embodiment, the reacting is performed for a time period in the range from 0.5-24 hours, preferably 1-12 hours, more preferably 2-8 hours, more preferably 4-6 hours. The reaction may be shaken/stirred throughout the duration of the reaction by employing a rotary shaker, a magnetic stirrer, or an overhead stirrer. In another embodiment, the reaction mixture is left to stand (i.e. not stirred). In one embodiment, the reaction mixture is preferably mixed in a centrifugal mixer with a rotational speed of at least 500 rpm, preferably at least 800 rpm, more preferably at least 1,000 rpm, even though it can also be mixed with a spatula. In one embodiment, the reaction mixture is sonicated during the mixing.

The reaction mixture is preferably heterogeneous and comprises suspended solid-supported catalyst particles in the liquid reaction mixture. In one embodiment, the solid-supported catalyst particles may be dispersed within the reaction mixture, and may further be filtered and recycled at the end of the reaction. In one embodiment, the solid-supported catalyst is placed in a bag or semi-permeable membrane and the bag is immersed in the reaction mixture.

Accordingly, the solid-supported catalyst remains in the bag or semi-permeable membrane until the coupling reaction is completed. The membrane that is required for this technique shall allow easy transportation of both reactants and products, yet have a pore size that ensures retention of the catalyst.

In certain embodiments, the progress of each reaction may be monitored by methods known to those skilled in the art, such as thin layer chromatography, gas chromatography, nuclear magnetic resonance, infrared spectroscopy, and high pressure liquid chromatography combined with ultraviolet detection or mass spectroscopy. Preferably, thin layer chromatography and gas chromatography combined with mass spectroscopy are used.

The palladium cross-coupling products and compounds obtained by the method of the present disclosure are isolated and purified by employing the aforementioned methods which are well-known to those skilled in the art. The isolated yield of the palladium cross-coupling product or derivatives thereof is at least 75%, preferably at least 80%, preferably at least 90%, more preferably at least 92%, based on the initial molar amount of the aryl halide. The palladium cross-coupling product or derivatives thereof, resulting either from a single run or a combination of runs, comprises less than 10 ppb palladium (measured by ICP-MS), preferably less than 5 ppb, more preferably less than 1 ppb, based on a total weight of the palladium cross-coupling product or derivatives thereof. In a preferred embodiment, less than less than 0.5% of the total palladium by weight on the solid-supported catalyst was leached into the products, preferably less than 0.25%, preferably less than 0.10%/0, preferably less than 0.05%, preferably less than 0.01%.

In a preferred embodiment, the method further comprises i) separating the catalyst composition from the palladium cross-coupling product or derivatives thereof to recover the catalyst composition, and ii) reusing the catalyst composition in at least 2 reaction cycles with a less than 5% decrease in at least one selected from the group consisting of catalytic activity, a molar yield of the palladium cross-coupling product, or a weight percentage of Pd metal relative to the total weight of the catalyst composition.

In certain embodiments, the solid-supported catalyst may be separated by removing the bag of solid-supported catalyst, dialysis in a solvent, or using a micro-filter or a paper filter. The phrase "recycling the solid-supported catalyst" refers to a process whereby the solid-supported catalyst or catalyst composition is first washed by an organic solvent, dried, and then added to a new batch of reactants (either for the same or a different type of coupling reaction). Preferred organic solvents for washing the solid-supported catalyst and/or dialysis may include, without limitation, methanol, acetone, ethanol, tetrahydrofuran, acetonitrile, dichloromethane, ether, glycol ether, acetamide, dimethyl acetamide, dimethyl sulfoxide, or combinations thereof. The solid-supported catalyst or catalyst composition may be dried in vacuum, and/or with heating, for example, the catalyst may be dried in a vacuum oven. Dried solid-supported catalyst or catalyst composition may be stored in a desiccator until the next run.

In a preferred embodiment, a turnover number of the catalyst composition after at least 8 reaction cycles, preferably at least 10 cycles, preferably at least 12 cycles, preferably at least 15 cycles more preferably at least 20 cycles, even more preferably at least 30 cycles is in the range of 1500-2500, preferably 1500-2000, preferably 1700-2000 and a turnover frequency of the catalyst composition after at least 8 reaction cycles, preferably at least 10 cycles, preferably at least 12 cycles, preferably at least 15 cycles more preferably at least 20 cycles, even more preferably at least 30 cycles in the range of 200-1500 cycles per hour, preferably 200-1000 cycles per hour, more preferably 200-500 cycles per hour In one embodiment, the solid-supported catalyst or catalyst composition is recycled for at least 2 reaction cycles, preferably at least 5 cycles, preferably at least 8 cycles, preferably at least 10 cycles, preferably at least 12 cycles, preferably at least 15 cycles more preferably at least 20 cycles, even more preferably at least 30 cycles. The catalyst composition may lose less than 5 wt %, preferably less than 2 wt %, more preferably less than 0.1 wt % of palladium (based on an initial amount of palladium present in the solid-supported catalyst and the total weight of the catalyst composition) after the solid-supported catalyst is used for at least 2 reaction cycles, preferably at least 10 cycles, more preferably at least 20 cycles, even more preferably at least 30 cycles. The yield of the palladium cross-coupling product from the coupling reaction may decrease less than 20 percentage points, preferably less than 10 percentage points, more preferably less than 5 percentage points, preferably less than 2 percentage points after the solid-supported catalyst is used for at least 2 reaction cycles, preferably at least 10 cycles, more preferably at least 20 cycles, even more preferably at least 30 cycles. The turnover number and the turnover frequency of the solid-supported catalyst or catalyst composition may decrease by less than 10%, preferably less than 5%, more preferably less than 2% after the solid-supported catalyst is used for at least 2 reaction cycles, preferably at least 10 cycles, more preferably at least 20 cycles, even more preferably at least 30 cycles.

In one embodiment, the catalytic composition or solid-supported catalyst may comprise the solid-supported catalyst ligand chelating rhodium and be employed in a chemical transformation such as a hydrogenation or hydroformylation. In one embodiment, the hydrogenation may be an asymmetric hydrogentation. Exemplary rhodium catalyzed hydrogenations include, but are not limited to, the hydrogenation of alkenes, the hydrogenation of alkynes, the hydrogenation of aromatic cyclic arenes, the hydrogenation of nitriles, and the hydrogenation of pyridines and N-heterocycles.

In one embodiment, the catalytic composition or solid-supported catalyst may comprise the solid-supported catalyst ligand chelating palladium and/or platinum and be employed in a chemical transformation such as the selective oxidation of alcohols and aldehydes or allylic alkylations. In one embodiment, the catalytic composition or solid-supported catalyst may comprise the solid-supported catalyst ligand chelating palladium or ruthenium and be employed in a chemical transformation such as Heck arylations and vinylations, Tsuji-Trost reactions (additions to π-allyls), olefin metathesis and/or aromatic carbon-heteroatom bond forming reactions.

The examples below are intended to further illustrate protocols for preparing and characterizing the solid-supported catalyst ligands and catalyst compositions of the present disclosure. Further, they are intended to illustrate assessing the properties of these materials and assessing their performance in palladium cross-coupling reactions. They are not intended to limit the scope of the claims.

Example 1

Synthesis of Bis(Oxazoline) Ligand 2,2'-(4-Iodo-benzene-1,2-diyl)bis(4,4-dimethyl-4,5-dihydro-1,3-oxazole) (BOX-1)

The iodo functionalized ligand (BOX-1) was prepared. FIG. 1 shows the scheme for this preparation starting from the reaction of 4-iodophthalonitrile with 2 mol equivalents of 2-amino-2-methyl-1-propanol. The BOX ligand was prepared in accordance with an earlier published procedure by the inventors for similar homogeneous catalysts [M. B. Ibrahim, B. El Ali, M. Fettouhi, L. Ouahab, *Appl. Organometal. Chem,* 2015, 29, 400.; and M. B. Ibrahim, S. M. Shakil Hussain, A. Fazal, M. Fettouhi, B. El Ali, *J. Coord. Chem.* 2015, 68:3, 432.; and S. M. Shakil-Hussein, M. B. Ibrahim, A. Fazal, R. Suleiman, M. Fettouhi and B. El Ali, *Polyhedron,* 2014, 70, 39.—each incorporated herein by reference in its entirety]. A solution of 4-iodophthalonitrile (4.0 mmol) and zinc triflate (5.0 mol %, 0.2 mmol) in dried chlorobenzene (30 mL) was stirred at room temperature for 15 minutes. A solution of 2-amino-2-methyl-1-propanol (8.0 mmol) in dry chlorobenzene (5 mL) was slowly added. The temperature was raised to 135° C. and the reaction mixture was refluxed for 24 hours. The solvent was removed using a rotary evaporator. The crude product was dissolved in 30 mL of dichloromethane and extracted twice with distilled water (2×20.0 mL). The aqueous layer was then separated and the combined organic layers were dried with anhydrous sodium sulfate. The dichloromethane was removed was removed using a rotary evaporator to obtain the impure product, which was then purified using silica gel column chromatography with dichloromethane-ether (4:1) as eluent.

Yield 94%; waxy solid; $^1$H NMR (500 MHz, CDCl$_3$) δ (ppm): 8.01 (s, 1H, C-3 aromatic), 7.73 (d, J=10 Hz, 1H, C-5 aromatic), 7.38 (d, J=10 Hz, 1H, C-6 aromatic), 3.99 (s, 2H, OCH$_2$), 3.98 (s, 2H, OCH$_2$), 1.30 (s, 6H, CH$_3$×2); 1.29 (s, 6H, CH$_3$×2); $^{13}$C NMR (125 MHz, CDCl$_3$) δ (ppm); 27.95 (CH$_3$×4), 67.92 (NCH×2), 79.40 (OCH$_2$×2), 96.12 (C-4 aromatic), 127.89 (C-1 aromatic), 130.11 (C-2 aromatic), 130.97 (C-6 aromatic), 138.26 (C-5 aromatic), 139.07 (C-3 aromatic), 160.82 (C-4'), 161.47 (C-1'); IR (KBr) υ (cm$^{-1}$) 2963, 2884, 1642, 1458, 1398, 1352, 1303, 1194, 1089, 1039, 964, 824, 723; GC-MS m/z 398 (M$^+$); Anal. Calc. for C$_{16}$H$_{19}$IN$_2$O$_2$ (398.24): C, 48.26; H, 4.81; N, 7.03. Found: C, 48.44; H, 4.88; N, 7.22.

Example 2

Synthesis of Hydroxyl Functionalized Bis(Oxazoline) Ligand 3,4'-Bis(4,4-dimethyl-4,5-dihydro-1,3-oxazole-2-yl)biphenyl-4-ol (BOX-2)

The hydroxyl functionalized ligand (BOX-2) was prepared from the Suzuki-Miyaura cross coupling reaction of BOX-1 with 4-hydroxyphenyl boronic acid (FIG. 1). 2,2'-(4-Iodobenzene-1,2-diyl)bis(4,4-dimethyl-4,5-dihydro-1,3-oxazole) (BOX-1) (0.50 mmol), PdCl$_2$ (0.025 mmol, 5.0 mol %), K$_2$CO$_3$ (1.0 mmol, 2.0 mol equivalent), DMF (2 mL), distilled water (2 mL) and 4-hydroxy phenylboronic acid (0.6 mmol), were added together in a 10 mL round bottom flask. The mixture was stirred at 70° C. for 6 hours. After completion of the reaction, the mixture was cooled down and acidified with 1M HCl. The acidified solution was extracted 3 times with Et-OAc and the combined Et-OAc extracts were dried using anhydrous MgSO4. The solvent was removed under reduced pressure and the product was purified by silica gel column chromatography using hexane-EtOAc (1:9) as an eluent.

Yield 94%; Light brown oil; $^1$H NMR (500 MHz, CDCl$_3$) δ (ppm): 7.81 (s, 1H), 7.79 (d, J=10 Hz, 1H), 7.57 (d, J=10 Hz, 1H), 7.25 (s, 2H), 6.82 (d, J=10 Hz, 2H), 4.18 (s, 2H, OCH$_2$), 4.14 (s, 2H, OCH$_2$), 1.51 (s, 6H, NC(CH$_3$)$_2$), 1.44 (s, 6H, NC(CH$_3$)$_2$); $^{13}$C NMR (125 MHz, CDCl$_3$) δ (ppm); 28.0 (NC(CH$_3$)$_2$), 28.1 (NC(CH$_3$)$_2$), 67.7 (NC(CH$_3$)$_2$), 67.9 (NC(CH$_3$)$_2$), 79.6 (OCH$_2$), 79.9 (OCH$_2$), 116.1, 116.2, 125.7, 127.9, 128.2, 130.3, 130.4, 143.4, 157.3, 162.5, 164.1; IR (CH$_2$Cl$_2$) υ (cm$^{-1}$) 3189, 2968, 2929, 2893, 1650, 1605, 1522, 1460, 1358, 1276, 1177, 1098, 964, 829. GC-MS m/z 364 (M$^+$); Anal. Calc. for C$_{22}$H$_{24}$N$_2$O$_3$ (364.44): C, 72.51; H, 6.64; N, 7.69. Found: C, 72.25; H, 6.38; I; N, 7.52.

Example 3

Synthesis of Supported Bis(Oxazoline) Ligand on Merrifield Resin (BOX-3) and Palladium (II) Bis (Oxazoline) Supported on Merrifield Resin (Pd-BOX)

Figure 2:
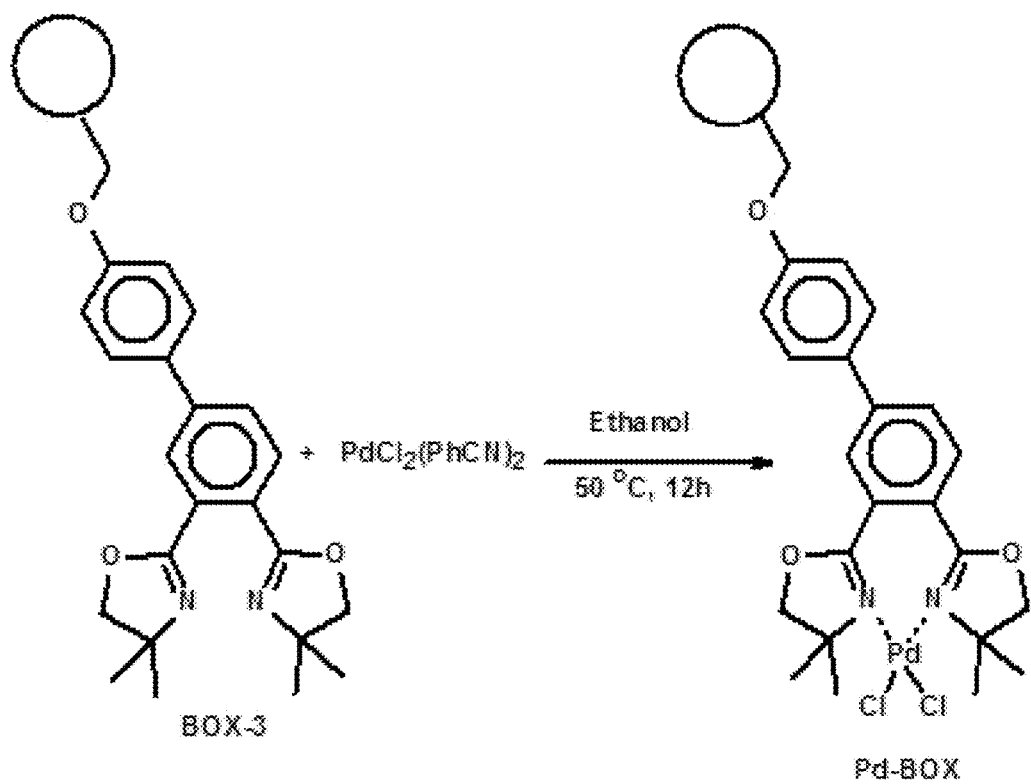
FIG. 2 is chemical reaction scheme for the synthesis of the catalyst composition wherein $R_1$ is —$CH_3$, $R_2$ is —$CH_3$, $R_3$ is —H, $R_4$ is —H, $R_5$ is —H, $R_6$ is —H, and X is O, the solid support, SS, is Merrifield resin, and the $Pd^{+2}$ species having the formula $PdZ_2$ is $PdCl_2$ (Pd-BOX) from the solid-supported catalyst ligand wherein $R_1$ is —$CH_3$, $R_2$ is —$CH_3$, $R_3$ is —H, $R_4$ is —H, $R_5$ is —H, $R_6$ is —H, and X is O, and the solid support, SS, is Merrifield resin (BOX-3).

The functionalization of Merrifield resin with the bis (oxazoline) ligand (BOX-2) to form Merrifield resin supported BOX ligand (BOX-3) (FIG. 1) followed by subsequent complexation with palladium chloride to form the polymer supported palladium bis(oxazoline) catalyst (Pd-BOX). FIG. 2 shows the shows the scheme for this preparation. NaH (0.5 mmol) was added in one portion to a stirred solution of 3,4'-Bis(4,4-dimethyl-4,5-dihydro-1,3-oxazole-2-yl)biphenyl-4-ol (BOX-2) (0.30 mmol) in dry DMF in a dry flask. The mixture was stirred for 2 hours at room temperature and under an argon atmosphere. Merrifield resin (0.30 mmol) was added and the mixture was stirred at 90° C. for 12 hours. The solid product was filtered and washed successively with methanol, water, acetone, and dichloromethane. The product was dried at room temperature under vacuum. Yellow solid; 91% yield; $^{13}$C NMR: δ 28.2, 41.7, 67.9, 80.3, 91.4, 120-140 (several signals), 168.8; IR: υ$_{max}$ (cm$^{-1}$) 3081, 3024, 2965, 2923, 1652, 1604, 1517, 1491, 1452, 1351, 1311, 1244, 1086, 1036, 825, 759, 699, Anal. C, 80.68; H, 6.36; N, 3.80.

The Merrifield resin supported bis(oxazoline) ligand (BOX-3) (0.3 mmol) was stirred in anhydrous ethanol for 30 minutes. An ethanolic solution of bis(benzonitrile) palladium (II) chloride (0.3 mmol) was added and the resulting mixture was stirred at 50° C. for 12 hours. The solid product was filtered, washed thoroughly with ethanol and dried in vacuum [M. Bakherad, B. Bahramian, H. Nasr-Isfahani, A. Kievanloo, G. Sang, Chin. *J. Chem.* 2009, 27, 353.—incorporated herein by reference in its entirety]. Dark brown solid, 95% yield; $^{13}$C NMR: δ 27.5, 41.4, 70.5, 81.7, 96.1, 120-140 (several signals), 182.3; IR: υ$_{max}$ (cm$^{-1}$) 3056, 3021, 2919, 2844, 1634, 1599, 1494, 1452, 1371, 1327, 1221, 1178, 1068, 1011, 950, 824, 757, 699; Anal. C, 62.84; H, 4.83; N, 2.99. Metal loading from ICP-MS: 6.7% corresponding to 0.6 mmol/g.

Example 4

Characterization and Analysis of Prepared Supported Bis(Oxazoline) Ligands, Intermediates and Supported Palladium Bis(Oxazoline) Catalysts The BOX ligands (BOX-1 and BOX-2) were characterized using analytical and spectroscopic techniques. The molecular weight of BOX-1 and BOX-2 were established using gas chromatography mass spectrometry (GC-MS). The $^1$H and $^{13}$C nuclear magnetic resonance (NMR) chemical shifts for the BOX ligands were consistent with their proposed structures and were in entire agreement with the characterization data of other known bis(oxazoline) ligands. The Fourier transform infrared (FT-IR) spectral data for both BOX-1 and BOX-2 ligands further confirmed their proposed structures. The formation of the expected supported bis(oxazoline) ligand on Merrifield resin (BOX-3) and palladium (II) bis(oxazoline) supported on Merrifield resin (Pd-BOX) products were confirmed by FT-IR, cross-polarization magic angle spinning nuclear magnetic resonance (CP-MAS NMR), elemental analysis and inductively coupled plasma mass spectrometry (ICP-MS).

The sharp C—Cl peak at 1264 cm$^{-1}$ which was observed in the FT-IR spectrum of the unmodified Merrifield resin is no longer present after the introduction of the bis(oxazoline) ligand and the complexation with palladium chloride. This is consistent with the fact that substantially all of the chloro groups attached to the resin were successfully replaced with the BOX ligand. The formation of the resin supported bis(oxazoline) ligand was further confirmed by the appearance of a strong band at 1652 cm$^{-1}$ without palladium and at 1634 cm$^{-1}$ due to the complexation with palladium. This peak was initially absent in the spectrum of the unmodified Merrifield resin. This band is attributed to the stretching of the imino (—C=N—) bond of the oxazoline ring. The shift in the position of the imino band ($\Delta v$=18 cm-1) confirms the coordination of palladium with the supported ligand. The position of the imino band in the supported ligand and the observed shift after coordination with palladium, entirely agrees with the previously reported literature [R. Antony, G. L. Tembe, M. Ravindranathan, R. N. Ram, *J. Appl. Polym. Sci.*, 2003, 90, 370.—incorporated herein by reference in its entirety].

Solid state NMR data of the polymer bound to the ligand and its palladium catalyst were in entire agreement with the data reported for other homogenous and supported bis(oxazoline) ligands and catalysts [M. S. Sarkar, M. L. Rahman, M. M. Yusoff, *RSC Adv.* 2015, 5, 1295.—incorporated herein by reference in its entirety]. The palladium loading on the polymer supported palladium catalyst which was analyzed using ICP-MS, was estimate as 6.7% (0.6 mmol/g). The thermal stability of both the resin supported ligand and its palladium catalyst was established from thermogravimetric analysis (TGA). The Merrifield resin supported bis(oxazoline) ligand and its palladium catalyst form were found to possess high thermal stability with a decomposition temperature greater than 350° C. In the X-ray photoelectron spectroscopy (XPS) spectrum of the supported catalyst, palladium peaks were observed in the range of 335 to 341 eV. Two distinctive 3d peaks were identified, the first peak with binding energy of 334.98 eV (Pd3d$_{5/2}$) and the second peak with binding energy of 340.28 (Pd3d$_{3/2}$). These peaks correspond to palladium (II) forms, and this confirms that palladium (II) is the main form of palladium in the supported catalyst.

Figure 3:
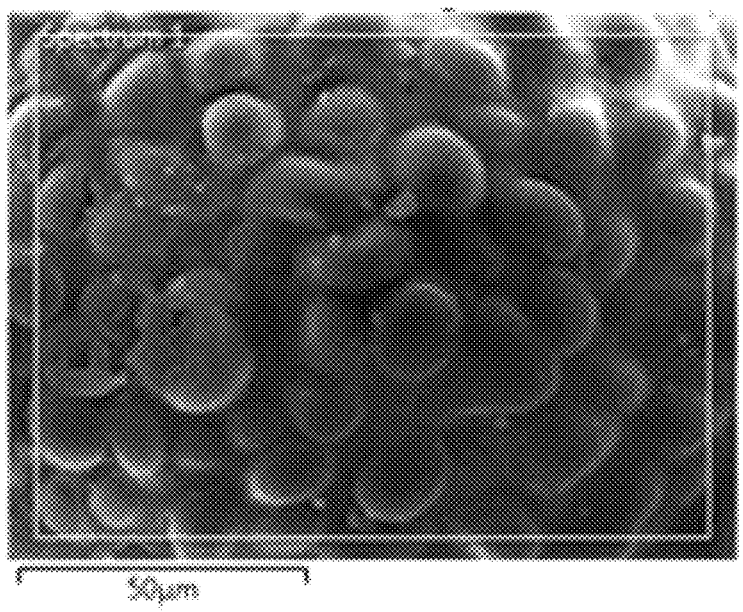
FIG. 3 is a scanning electron microscopy (SEM) image of a single bead of pure unfunctionalized Merrifield resin.
Figure 4:
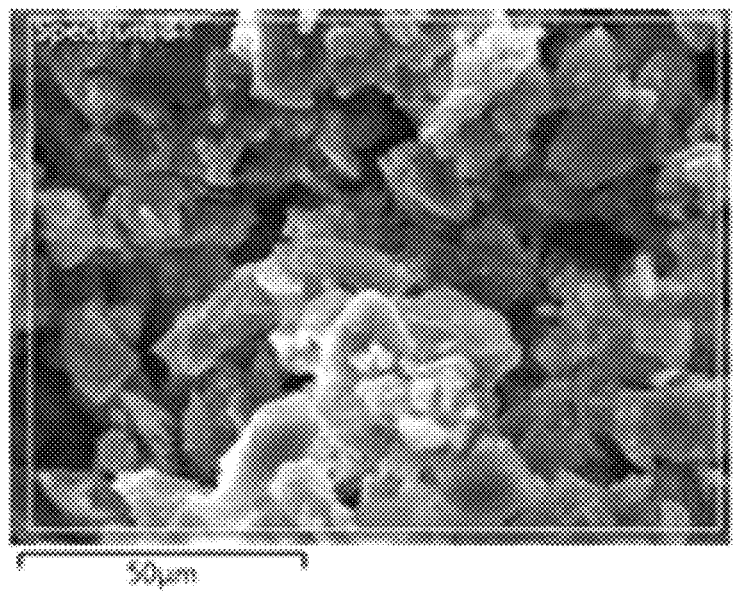
FIG. 4 is a SEM image of the solid-supported catalyst ligand wherein $R_1$ is —$CH_3$, $R_2$ is —$CH_3$, $R_3$ is —H, $R_4$ is —H, $R_5$ is —H, $R_6$ is —H, and X is O, and the solid support, SS, is Merrifield resin (BOX-3).
Figure 5:
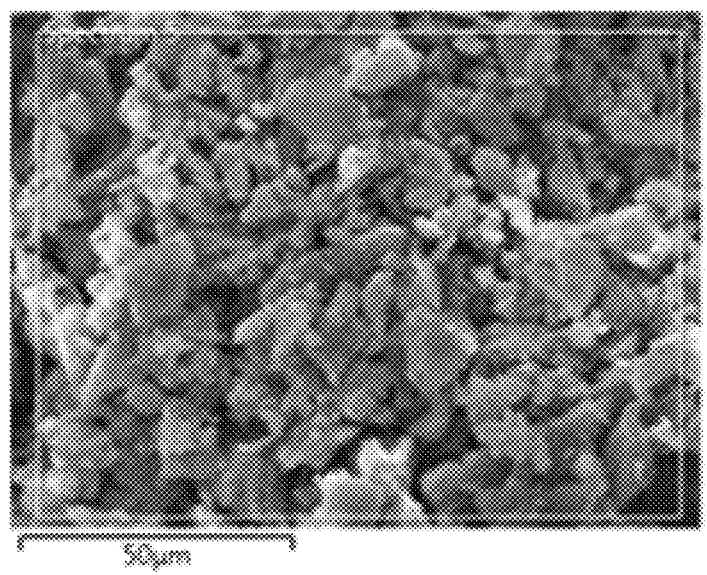
FIG. 5 is a SEM image of the catalyst composition wherein $R_1$ is —$CH_3$, $R_2$ is —$CH_3$, $R_3$ is —H, $R_4$ is —H, $R_5$ is —H, $R_6$ is —H, and X is O, the solid support, SS, is Merrifield resin, and the $Pd^{+2}$ species having the formula $PdZ_2$ is $PdCl_2$ (Pd-BOX).

In order to assess the morphology of the Merrifield resin, Merrifield resin supported bis(oxazoline) ligand (BOX-3) and the Merrifield resin supported dichloridopalladium (II) bis(oxazoline) complex (Pd-BOX), scanning electron microscopy (SEM) micrographs were recorded for a single bead of pure Merrifield resin (FIG. 3), the supported bis(oxazoline) ligand (FIG. 4), and the supported dichloridopalladium (II) catalyst (FIG. 5). Expectedly, the smooth and flat microsphere surfaces of the Merrifield resin have been broken into a rough and irregular surface after incorporation of the bis(oxazoline) ligand and then the palladium bis(oxazoline) catalyst. The morphological changes observed were similar to what has been previously reported in the literature for other polystyrene supported ligands and their palladium catalyst [M. Bakherad, A. Keivanloo, B. Bahramian, S. Jajarmi, *Appl. Catal. A: General* 2010, 390, 135.—incorporated herein by reference in its entirety].

Example 5

Catalytic Activity of Palladium Bis(Oxazoline) Supported on Merrifield Resin (Pd-BOX) in Suzuki-Miyaura Cross Coupling Reactions The activity of the prepared supported catalyst in the Suzuki-Miyaura cross coupling reaction of arylboronic acids and aryl halides was carefully examined. In general, the Suzuki-Miyaura coupling reaction, which is catalyzed by supported palladium catalysts, follows a similar mechanism to that of the homogeneous catalyst [M. S. Sarkar, M. L. Rahman, M. M. Yusoff, *RSC Adv.* 2015, 5, 1295.—incorporated herein by reference in its entirety]. For this reason, previously optimized reaction conditions were adopted based on homogeneous palladium bis(oxazoline) catalysts ([Pd]/K$_2$CO$_3$/DMF-H$_2$O). Several arylboronic acids with aryl iodides, aryl bromides, and aryl chlorides were considered in this reaction.

In a general procedure for Suzuki-Miyaura cross coupling reaction aryl halide (1.0 mmol), aryl boronic acid (1.2 mmol), potassium carbonate (2.0 mmol), DMF (3.0 mL) and distilled water (3.0 mL) were added together in a 10 mL round bottom flask. Immobilized palladium bis(oxazoline) catalyst contained in a dialysis bag (0.0050 mmol) was introduced. The mixture was stirred at 80° C. The progress of the reaction was monitored by gas chromatography. After completion of the reaction, the catalyst bag was removed and dialyzed in DMF to extract all the products. The combined solutions were extracted with ethyl acetate. The combined ethyl acetate extracts were dried over anhydrous magnesium sulfate. The solvent was removed under reduced pressure using a rotary evaporator. The crude product was purified by silica gel column chromatography using hexane-EtOAc as eluent.

Figure 6:
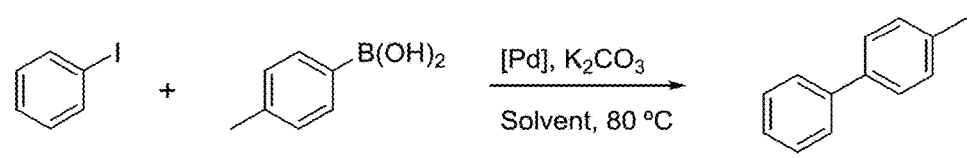
FIG. 6 is a chemical reaction scheme for the reaction of iodobenzene with p-tolylboronic acid in the palladium cross-coupling Suzuki-Miyaura reaction.
Figure 7:
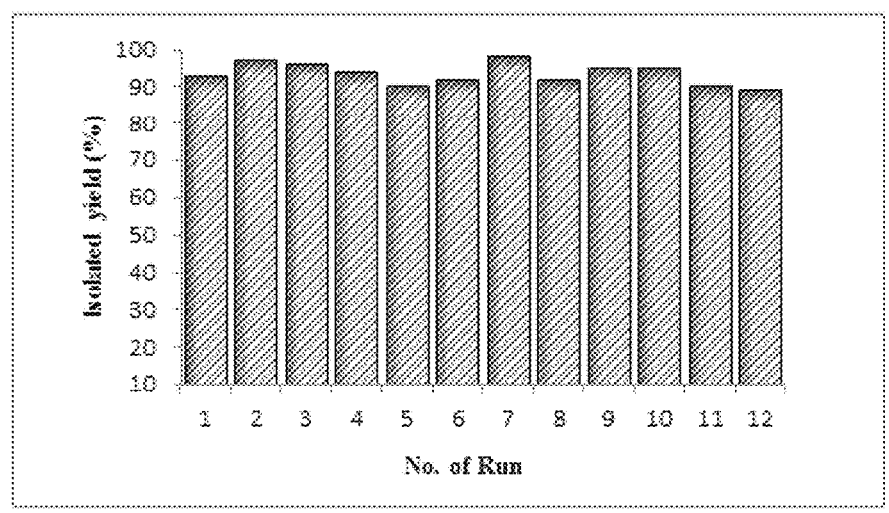
FIG. 7 is a graph illustrating the isolated yields and recycling ability of the palladium cross-coupling Suzuki-Miyaura reaction of iodobenzene with p-tolylboronic acid in the presence of the catalyst composition wherein $R_1$ is —$CH_3$, $R_2$ is —$CH_3$, $R_3$ is —H, $R_4$ is —H, $R_5$ is —H, $R_6$ is —H, and X is O, the solid support, SS, is Merrifield resin, and the $Pd^{+2}$ species having the formula $PdZ_2$ is $PdCl_2$ (Pd-BOX) with 0.0050 mmol [Pd], 1.5 mmol p-tolylboronic acid, 1.0 mmol iodobenzene, and 2.0 mmol $K_2CO_3$ in 3.0 mL DMF and 3.0 mL $H_2O$ at 80° C. for 2 hours.

The recycling ability of the prepared supported palladium bis(oxazoline) catalyst in DMF-H$_2$O was investigated in the Suzuki-Miyaura cross coupling reaction of iodobenzene with p-tolylboronic acid at 80° C. for 2 hours (FIG. 6). The supported catalyst was packaged in a membrane tube fabricated from a commercially available dialysis bag. The membrane allows the migration of molecules with low molecular weight. This means that only the reactants and products can smoothly pass through it. The transport of both reactants and products into and out of the membrane is driven by the concentration gradient and temperature of the reaction (80° C.) [M. Gaab, S. Bellemin-Laponnaz, L. H. Gade, *Chem. Eur. J.* 2009, 15, 5450.; and J. S. Willemsen, J. C. M. Van-Hest, F. P. J. T. Rutjes, *Beilstein J. Org. Chem.* 2013, 9, 960.—each incorporated herein by reference in its entirety]. FIG. 7 presents the results of the recycling experiments. Remarkably, the supported catalyst could be recycled up to twelve times without bearing any loss in its catalytic activity. The turnover number was estimated for the 12 reaction cycles as 2242, while the turnover frequency was estimated as 1121/h. In order to confirm the efficiency of the supported catalyst, an experimental run was conducted with a ratio of iodobenzene (12.0 mmol) to supported palladium bis(oxazoline) catalyst (0.005 mmol) equal to 2400 for 2 hours. A complete conversion of iodobenzene and an excellent isolated yield (98%) of the coupling product was obtained. The turnover number of the supported palladium-bis(oxazoline) catalyst in this experimental run was estimated as 2353, while the turnover frequency was estimated as 1176/h.

Previous studies by the inventors have established that the homogeneous Pd-BOX complexes exhibit high activities for the Suzuki-Miyaura coupling of diversely functionalized aryl halides including aryl iodide, aryl bromides, and aryl chlorides with a wide array of arylboronic acids. It has been found that the homogeneous catalytic system is tolerant to a wide variety of functional groups on both the aryl halides and the arylboronic acids. Previous studies related to the recycling ability of supported catalysts are restricted to the reaction of the same substrates throughout the catalytic cycles. In contrast, the present disclosure establishes a new method by recycling the used catalyst for all coupling reactions of different substrates. This means the same palladium-BOX supported catalyst placed in a dialysis bag was used for all substrates indicated in the Table 1. Table 1 presents the Suzuki-Miyaura coupling reaction of various aryl halides with different arylboronic acids using the prepared Pd-BOX supported catalyst. The recycling ability of the prepared palladium supported catalyst was applied in the Suzuki-Miyaura cross coupling of a broad range of substrates using DMF-$H_2O$ (1:1) as a solvent system and $K_2CO_3$ as a base. Thus, different aryl halides including aryl iodides, aryl bromides and aryl chlorides were coupled successfully with various arylboronic acids (Table 1). At the end of each reaction, the catalyst contained in a dialysis bag was removed from the reaction mixture, dialyzed in DMF to remove all the traces of reactants and products, and dried under open air conditions before being used in the next catalytic reaction with a new substrate.

TABLE 1

Results of Suzuki-Miyaura coupling reactions of various aryl halides with different arylboronic acids using the prepared Pd-BOX supported catalyst

| Entry | Aryl Halide | Aryl Boronic Acid | Time (h) | Yield (%)[b] |
|---|---|---|---|---|
| 1 | 4-acetylphenyl-I | phenyl-B(OH)$_2$ | 2 | 96 |
| 2 | 4-nitrophenyl-I | phenyl-B(OH)$_2$ | 2 | 94 |
| 3 | phenyl-I | benzo[d][1,3]dioxol-5-yl-B(OH)$_2$ | 2 | 95 |
| 4 | 4-methoxyphenyl-I | phenyl-B(OH)$_2$ | 4 | 92 |
| 5 | 4-acetylphenyl-Br | phenyl-B(OH)$_2$ | 3 | 94 |
| 6 | 4-methylphenyl-Br | phenyl-B(OH)$_2$ | 5 | 90 |
| 7[c] | 4-formylphenyl-Cl | phenyl-B(OH)$_2$ | 12 | 95 |
| 8[c] | phenyl-Cl | 4-ethoxyphenyl-B(OH)$_2$ | 12 | 92 |

[a]Reaction Conditions: [Pd] (0.005 mmol), aryl boronic acid (1.2 mmol), aryl halide (1.0 mmol), $K_2CO_3$ (2.0 mmol), DMF (3.0 mL), $H_2O$ (3.0 mL), 80° C.
[b]Isolated Yield.
[c]110° C., using fresh catalyst.

Aryl iodides having either activating or deactivating groups reacted smoothly, affording the cross coupling products in excellent isolated yields (92-98%) (Table 1, entries 1-4). Various functional groups were tolerated with the prepared palladium supported catalysts. The coupling reactions were also successful with both activated and deactivated aryl bromides leading to the corresponding biphenyl products in high isolated yields (Table 1, entries 5-6). It is of note that all the reactions of arylboronic acids with aryl iodides and aryl bromides were conducted with the same recycled catalyst. Aryl chlorides were less reactive as anticipated and the reactions required a relatively higher temperature (110° C.). The coupling reactions of aryl chlorides were conducted using a solid fresh catalyst and without dialysis bag. In addition, a longer reaction time (12 hours) was necessary to obtain high yields (Table 1, entries 7-8). The effect of varying the substituents on the arylboronic acids was also investigated. In contrast to aryl halides, the overall electronic effect of the arylboronic acids with the supported palladium bis(oxazoline) catalyzed Suzuki-Miyaura reaction was rather insignificant.

Example 6

Catalytic Activity of Palladium Bis(Oxazoline) Supported on Merrifield Resin (Pd-BOX) in Mizoroki-Heck Cross Coupling Reactions The catalytic activities of the prepared supported palladium bis(oxazoline) catalyst in Mizoroki-Heck coupling reactions of various olefins and aryl halides was carefully examined. Previously optimized reaction conditions were adopted based on homogeneous palladium bis(oxazoline) catalysts ([Pd]/KOH/DMF-$H_2O$). In a general procedure for Mizorok-Heck cross coupling reactions a mixture of aryl halide (1.0 mmol), alkene (1.5 mmol), KOH (2.0 mmol), DMF (2.0 mL) and distilled water (2.0 mL) was added together in a 10 mL round bottom flask. Immobilized palladium bix(oxazoline) catalyst contained in a dialysis bag (0.0050 mmol) was introduced. The mixture was stirred at 80° C. The progress of the reaction was monitored by gas chromatography. After the completion of the reaction, the catalyst bag was removed and dialyzed in DMF to extract all the products. The combined solutions were extracted with ethyl acetate. The combined ethyl acetate extracts were dried over anhydrous magnesium sulfate. The solvent was removed under reduced pressure using a rotary evaporator. The crude product was purified by silica gel column chromatography using hexane-EtOAc as an eluent.

Figure 8:
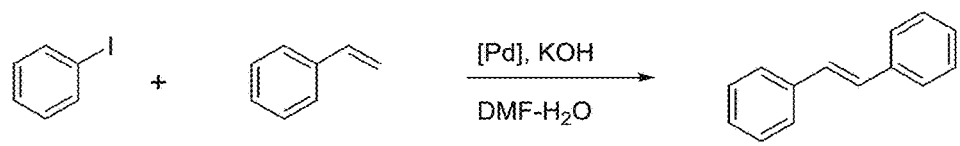
FIG. 8 is a chemical reaction scheme for the reaction of iodobenzene with styrene in the palladium cross-coupling Mizoroki-Heck reaction.
Figure 9:
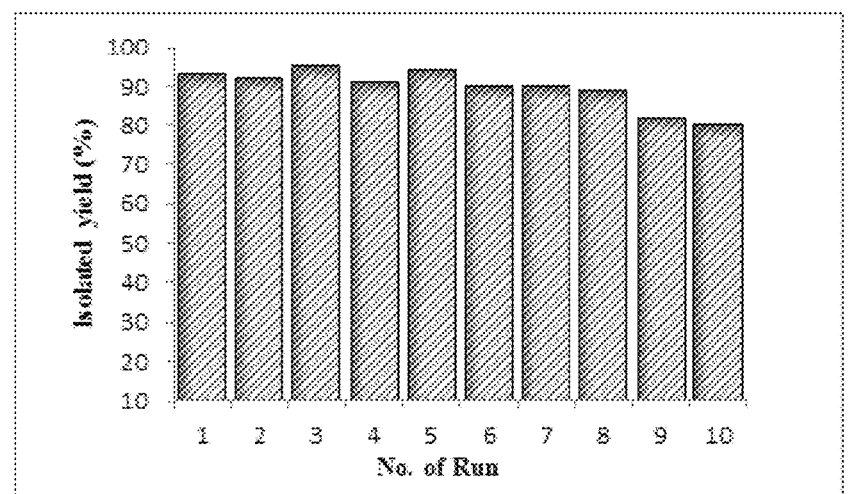
FIG. 9 is a graph illustrating the isolated yields and recycling ability of the palladium cross-coupling Mizoroki-Heck reaction of iodobenzene with styrene in the presence of the catalyst composition wherein $R_1$ is —$CH_3$, $R_2$ is —$CH_3$, $R_3$ is —H, $R_4$ is —H, $R_5$ is —H, $R_6$ is —H, and X is O, the solid support, SS, is Merrifield resin, and the $Pd^{+2}$ species having the formula $PdZ_2$ is $PdCl_2$ (Pd-BOX) with 0.0050 mmol [Pd], 1.5 mmol styrene, 1.0 mmol iodobenzene, and 2.0 mmol KOH in 3.0 mL DMF and 3.0 mL $H_2O$ at 80° C. for 6 hours.

The recycling ability of the prepared Merrifield resin supported palladium bis(oxazoline) catalyst in the Mizoroki-Heck coupling reaction of iodobenzene with styrene was examined (FIG. 8). Interestingly, the supported catalyst could be recycled up to 10 times without significant loss in its catalytic activity. FIG. 9 presents the results of the recycling experiments. The turnover number of the Merrifield resin supported palladium bis(oxazoline) catalyst was estimated for the 10 reaction cycles as 1800, while the turnover frequency was found to be 300/h. In order to confirm the efficiency of the Merrifield resin supported palladium bis(oxazoline) catalyst, an experimental run was conducted with a ratio of iodobenzene (10.0 mmol) to supported palladium bis(oxazoline) catalyst (0.005 mmol) equal to 2000 for 6 hours. A substantially complete conversion of iodobenzene and excellent isolated yield of product (93%) was observed. The turnover number of the Merrifield resin supported palladium bis(oxazoline) catalyst in this experimental run was estimated as 1860, while the turnover frequency was found as 310/h.

Previous studies by the inventors have reported that the homogeneous palladium bis(oxazoline) catalysts exhibit high catalytic activity for the Mizoroki-Heck coupling reaction of diversely functionalized aryl iodides with a wide array of terminal alkenes. The homogeneous palladium bis(oxazoline) catalyst previously reported, was capable of tolerating a variety of functional groups on both the aryl iodides and the alkenes. The high recycling ability realized with the prepared supported catalyst in the Mizoroki-Heck cross coupling of iodobenzene with styrene encouraged an examination of the recycling ability of the supported catalysts in the Mizoroki-Heck coupling of a broad range of substrates using DMF-$H_2O$ (1:1) as a solvent system and KOH as a base. Thus, various aryl halides including aryl iodides and aryl bromides were coupled successfully with various styrene derivatives. Table 2 presents the Mizoroki-Heck coupling reaction of various aryl halides with different alkenes using the prepared Pd-BOX supported catalyst. At the end of each reaction, the catalyst was removed from the reaction mixture and dialyzed in DMF to remove all traces of reactants and products before being taken forward into a subsequent catalytic reaction run.

TABLE 2

Results of Mizorok-Heck coupling reactions of various aryl halides with different alkenes using the prepared Pd-BOX supported catalyst

| Entry | Aryl Halide | Alkene | Coupling Product | Yield (%)[b] |
|---|---|---|---|---|
| 1 | iodobenzene | styrene | stilbene | 96 |
| 2 | iodobenzene | 4-methoxystyrene | 4-methoxystilbene | 96 |
| 3 | 4-iodoanisole | styrene | 4-methoxystilbene | 90 |

TABLE 2-continued

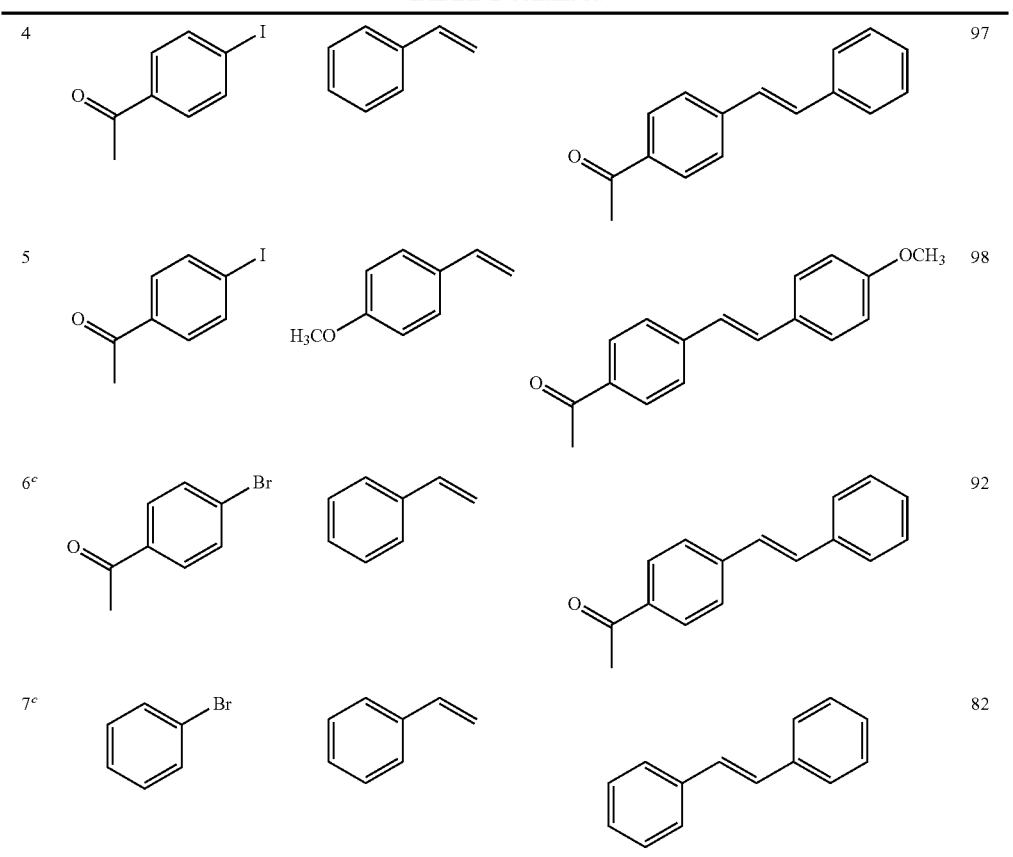

<sup>a</sup>Reaction Conditions: [Pd] (0.005 mmol), alkene (1.5 mmol), aryl halide (1.0 mmol), KOH (2.0 mmol), DMF (3.0 mL), H₂O (3.0 mL), 80° C., 6 hours.
<sup>b</sup>Isolated Yield.
<sup>c</sup>reacted at 110° C.

Example 7

Catalytic Activity of Palladium Bis(Oxazoline) Supported on Merrifield Resin (Pd-BOX) in Sonogashira Cross Coupling Reactions The catalytic activities of the prepared supported palladium bis(oxazoline) catalysts in Sonogashira cross coupling reactions of alkynes and aryl halides was investigated. Previously optimized reaction conditions were adopted based on the catalytic system of homogeneous palladium bis(oxazoline) catalysts ([Pd]/KOH/CH₃CN—H₂O) [M. B. Ibrahim, B. El Ali, I. Malik, M. Fettouhi, *Tetrahedron. Lett.* 2015, 57, 554.—incorporated herein by reference in its entirety]. The coupling reactions of various aryl iodides with aryl and alkyl alkynes were considered in this reaction. In a general procedure for Sonogashira cross coupling reactions a mixture of aryl halide (1.0 mmol), alkyne (1.5 mmol), KOH (2.00 mmol), acetonitrile (2 mL) and distilled water (2 mL) were added together to a flask. Immobilized palladium bis(oxazoline) catalyst contained in a dialysis bag (0.0050 mmol) was introduced. The mixture was stirred at 60° C. for the required time. After completion of the reaction, the catalyst bag was removed and dialyzed in acetonitrile to extract all the products. The combined solutions were extracted with ethyl acetate. The combined ethyl acetate extracts were dried over anhydrous magnesium sulfate. The solvent was removed under reduced pressure in a rotary evaporator. The residue was purified using column chromatography with hexane-EtOAc as eluent to afford the cross coupling product in an excellent yield.

Figure 10:
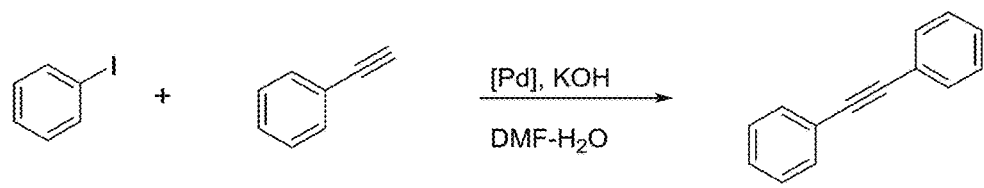
FIG. 10 is a chemical reaction scheme for the reaction of iodobenzene with phenylacetylene in the palladium cross-coupling Sonagashira reaction.
Figure 11:
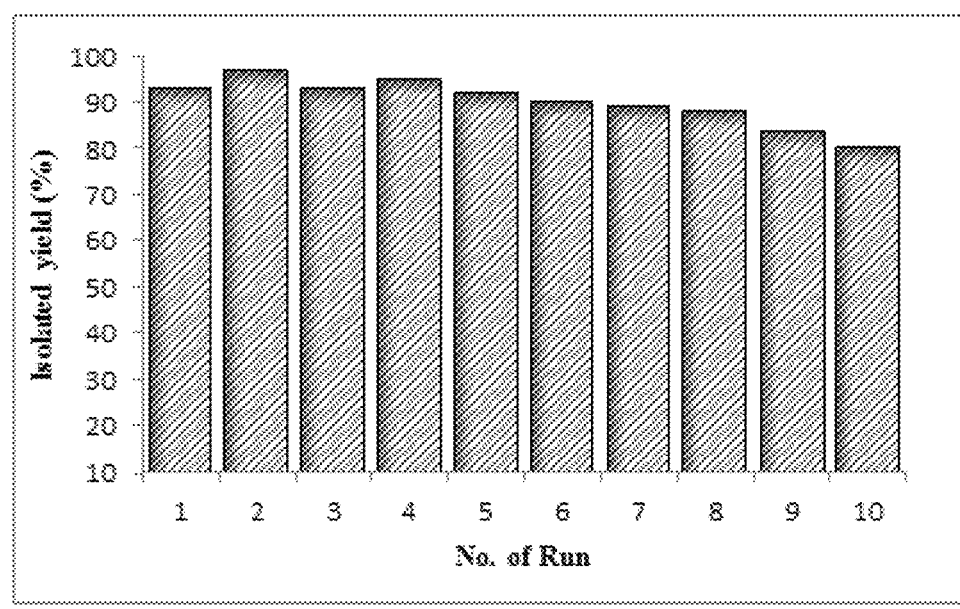
FIG. 11 is a graph illustrating the isolated yields and recycling ability of the palladium cross-coupling Sonogashira reaction of iodobenzene with phenylacetylene in the presence of the catalyst composition wherein $R_1$ is —$CH_3$, $R_2$ is —$CH_3$, $R_3$ is —H, $R_4$ is —H, $R_5$ is —H, $R_6$ is —H, and X is O, the solid support, SS, is Merrifield resin, and the $Pd^{+2}$ species having the formula $PdZ_2$ is $PdCl_2$ (Pd-BOX) with 0.0050 mmol [Pd], 1.5 mmol phenylacetylene, 1.0 mmol iodobenzene, and 2.0 mmol KOH in 2.0 mL acetonitrile and 2.0 mL $H_2O$ at 60° C. for 6 hours.

The recycling ability of the prepared Merrifield resin supported palladium bis(oxazoline) catalyst in the Sonogashira cross coupling reaction of iodobenzene with phenylacetylene was examined (FIG. 10). Interestingly, the supported catalyst could be recycled up to ten times without significant loss in its catalytic activity. FIG. 11 presents the results of the recycling experiments. The turnover number of the supported palladium bis(oxazoline) catalyst was estimated for the 10 reaction cycles as 1802, while the turnover frequency was found to be 300/h. In order to confirm the efficiency of the supported palladium bis(oxazoline) catalyst, an experimental run was conducted with a ratio of iodobenzene (10.0 mmol) to supported palladium bis(oxazoline) catalyst (0.005 mmol) equal to 2000 for 6 hours. A substantially complete conversion of iodobenzene and an excellent isolated yield of product (96%) were observed. The turnover number of the supported palladium bis(oxazoline) catalyst in this experimental run was estimated as 1920 while the turnover frequency was found to be 320/h.

The high recycling ability of the supported palladium bis(oxazoline) catalyst in the Sonogashira cross coupling reaction of iodobenzene with phenylacetylene suggested an extension of the scope of the coupling reaction to various electronically different aryl halides and alkynes. Table 3 presents the Sonogashira coupling reaction of various aryl halides with different alkynes using the prepared Pd-BOX supported catalyst. The Sonogashira coupling reaction of 4-iodoacetophenone with phenylacetylene was studied using the Merrifield resin supported palladium bis(oxazoline) catalyst. The corresponding internal acetylene was obtained in almost quantitative yield (95%) (Table 3, entry 1). The catalyst was dialyzed in acetonitrile and the purified catalyst was used again for the coupling of iodobenzene with p-tolylacetylene. Interestingly, the reaction worked to give excellent yield (90%) of the expected product (Table 3, entry 2). The same catalyst was then used in the coupling of phenylacetylene with 4-iodoanisole and with 4-iodoaniline (Table 3, entries 4 and 5). The corresponding internal acetylenes were also isolated in excellent yields (89% and 90%, respectively). The recycled catalyst was also evaluated in the Sonogashira coupling reaction of iodobenzene with alkyl alkynes. For example, the coupling reaction of iodobenzene with 5-chloro-1-pentyne led to excellent yield (91%) of the coupling product (Table 3, entry 6). Similarly, 5-cyano-1-pentyne was successfully coupled with iodobenzene (93%) (Table 3, entry 7).

TABLE 3

Results of Sonogashira coupling reactions of various aryl halides with different alkynes using the prepared Pd-BOX supported catalyst

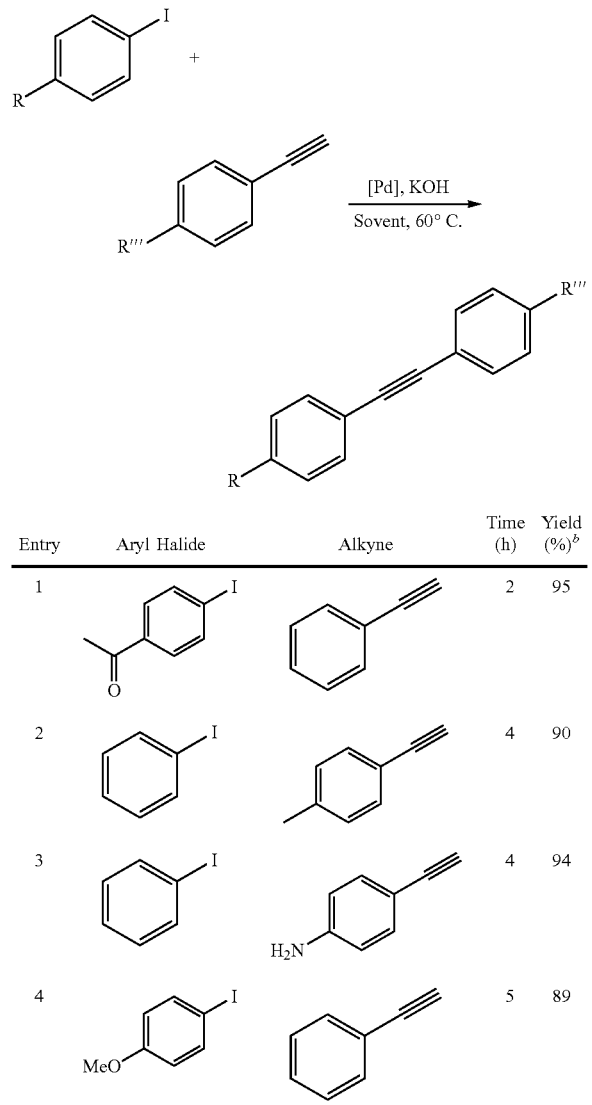

<sup>a</sup>Reaction Conditions: [Pd] (0.005 mmol), alkyne (1.5 mmol), aryl halide (1.0 mmol), KOH (2.0 mmol), CH$_3$CN (2.0 mL), H$_2$O (2.0 mL), 60° C.
<sup>b</sup>Isolated Yield.

Example 8

General Procedure for and Characterization and Analysis of the Recycling of the Prepared Supported Palladium Bis(Oxazoline) Catalysts Using a Dialysis Bag The reusability of the supported palladium bis(oxazoline) catalyst was studied in a number of cross coupling reactions including the Suzuki-Miyaura, Mizoroki-Heck, and Sonogashira cross coupling reactions. In this procedure membrane piece was soaked in distilled water for 5 minutes and squeezed open. The bag was tied from the bottom. The required quantity of the catalyst and a magnetic stir bar were placed in the bag. The bag was then tied from the top. The catalyst bag was placed in a flask containing the appropriate reactants. The flask was mounted on a hot plate equipped with magnetic stirring. At the end of each reaction cycle, the catalyst bag was removed from the reaction flask and dialyzed in the appropriate solvent to remove all traces of the reactants and product. The catalyst bag was then placed in another flask containing fresh substrates for the subsequent run. The same cleaning procedure was repeated after each cycle. After the sixth cycle, the catalyst was removed from the dialysis bag, washed successively with water, acetone, and methanol. The catalyst was dried in an oven at 100° C. and then place in a new dialysis bag and used in the subsequent cycles.

It was further necessary to characterize the recycled palladium bis(oxazoline) supported catalysts. The ability to recycle the Merrifield resin supported palladium bis(oxazoline) catalyst for several reaction cycles and in various cross coupling reactions without significant loss in its catalytic activity demonstrates its high stability and catalytic activity. The outstanding results obtained with the supported catalysts suggested a further investigation in order to examine and determine the change in the structure and composition of the used catalyst, if any, as compared with the fresh catalyst. The recovered catalysts from the various cross coupling reactions were washed successively with distilled water, acetone, and methanol. The catalysts were then dried in an oven at 100° C. prior to the analysis. The washed catalysts were analyzed using FT-IR and XPS and the amount of palladium loading was established using ICP-MS.

The FT-IR spectrum of the recovered Merrifield resin supported catalyst was found to be similar with the spectrum of the un-used catalyst. The percentage of palladium on the supported catalyst recovered from the Suzuki-Miyaura (6.0%) and the Mizorok-Heck (6.1%) cross coupling reaction was found to be almost similar to the amount of palladium loading in the fresh catalyst (6.7%). These results further justify the high recycling ability observed with the new supported catalysts. The XPS spectrum of the recovered catalyst shows that the oxidation state of palladium remains unchanged after the catalytic applications. Similar to the un-used supported catalyst, the 3d spectrum, resolved in to $3d_{5/2}$ and $3d_3R$ spin orbit pairs with binding energies of 334.58 eV and 339.78 eV respectively [H. N. Yeap, W. Mian, H. Hong, L. L. C. Christina, Chem. Commun., 2009, 5530.; and A. R. Hajipour, Z. Shirdashtzade, G. Azizi, J. Chem. Sci. 2014, 126, 1, 85.—each incorporated herein by reference in its entirety].

In addition, leaching tests of the palladium bis(oxazoline) supported catalysts were performed. The main objective of supporting a homogeneous catalyst is to enable its easy separation from the product and to minimize the level of contamination caused by leaching of the toxic metal. The possibility of palladium leaching into the products was analyzed using ICP-MS. After recycling the catalyst, the solutions from the reaction were combined in various containers. The solution in each container was digested separately using concentrated nitric acid and were analyzed using ICP-MS. The results from the ICP-MS analysis indicate that the concentration of palladium in the products was below 10 ppb in each sample. These results indicate that less than 0.5% of the total palladium on the supported catalyst was leached into the products. This clearly indicates the high stability of the catalyst towards the cross coupling reactions under the current prescribed conditions.

A new palladium (II) bis(oxazoline) supported on Merrifield resin (Pd-BOX) as heterogeneous catalyst was synthesized and characterized. The new supported Pd-BOX catalyst showed excellent catalytic activity in different cross coupling reactions including Suzuki-Miyaura, Mizaroki-Heck, and Sonogashira reactions. The excellent catalytic activity of the supported Pd-BOX catalyst was reflected by the high recycling ability for more than 10 cycles without a significant loss in the activity. Various biaryl, internal alkene and alkyne compounds have been synthesized in excellent isolated yields. The catalytic system can tolerate a wide range of substituents on the reactant aryl halides, aryl boronic acids, styrene alkene derivatives and alkynes. The characterization data of the used catalyst was found to be similar if not practically the same as that of the un-used catalyst, which reflects the high stability of the new heterogeneous palladium catalyst. These new materials reported in this disclosure and prepared using the new palladium catalyst system could be of high interest to most electronic displays, petrochemical and chemical feedstocks companies.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A solid-supported catalyst, comprising:
a catalytic metal in the form of a $Pd^{+2}$ species having the formula $PdZ_2$, wherein Z is selected from the group consisting of —Cl, —I, —Br, —OAc, and —OTf, and
a solid-supported ligand of formula (I)

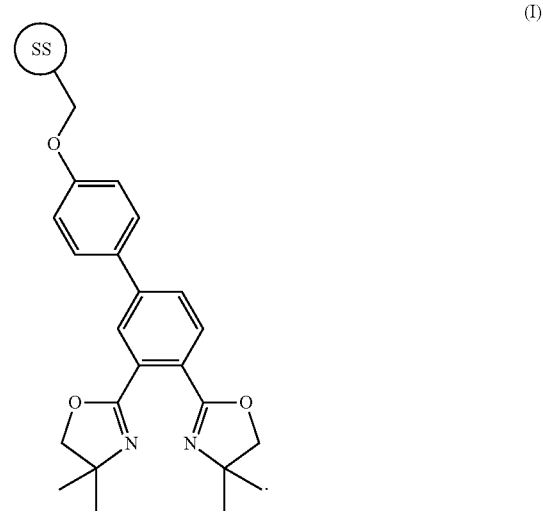

wherein the nitrogen atoms of the two oxazoline heterocycles of the solid-supported ligand chelate the catalytic metal; and
wherein SS is a solid resin bead with the proviso that the solid resin bead is not silica.

2. The solid-supported catalyst of claim 1, wherein the solid resin bead is Merrifield resin.

3. The solid-supported catalyst of claim 1, wherein the solid-supported catalyst is in the form of a particle having an average particle size in terms of an average diameter of 1-100 μm.

4. The solid-supported catalyst of claim 1, wherein the $Pd^{+2}$ species having the formula $PdZ_2$ is $PdCl_2$.

5. The solid-supported catalyst of claim 1, which comprises 0.05-1.5 mmol of palladium per gram of the catalyst composition.

6. The solid-supported catalyst of claim 1, which has a turnover number in a range of 1500-2500 and a turnover frequency in a range of 200-1500 per hour.

* * * * *